(12) United States Patent
Mandaroux et al.

(10) Patent No.: US 11,890,457 B2
(45) Date of Patent: Feb. 6, 2024

(54) ASPIRATION AND INJECTION DEVICE

(71) Applicant: Allergan, Inc., Irvine, CA (US)

(72) Inventors: Bastien Mandaroux, Metz-Tessy (FR); Shushuo Wu, Thousand Oaks, CA (US); Lance Hussey, Thousand Oaks, CA (US)

(73) Assignee: Allergan, Inc., Irvine, CA (US)

( * ) Notice: Subject to any disclaimer, the term of this patent is extended or adjusted under 35 U.S.C. 154(b) by 711 days.

(21) Appl. No.: 16/798,153

(22) Filed: Feb. 21, 2020

(65) Prior Publication Data

US 2020/0188599 A1    Jun. 18, 2020

Related U.S. Application Data

(63) Continuation of application No. 15/469,004, filed on Mar. 24, 2017, now Pat. No. 10,596,321.

(60) Provisional application No. 62/320,281, filed on Apr. 8, 2016.

(51) Int. Cl.
| | |
|---|---|
| *A61M 5/31* | (2006.01) |
| *A61M 5/178* | (2006.01) |
| *A61M 5/315* | (2006.01) |
| *A61B 17/00* | (2006.01) |

(52) U.S. Cl.
CPC ...... *A61M 5/3137* (2013.01); *A61M 5/31505* (2013.01); *A61M 5/31511* (2013.01); *A61M 5/31513* (2013.01); *A61B 2017/00792* (2013.01); *A61M 5/1782* (2013.01); *A61M 2005/3139* (2013.01); *A61M 2005/31508* (2013.01); *A61M 2205/586* (2013.01); *A61M 2207/00* (2013.01)

(58) Field of Classification Search
CPC .............. A61M 5/3137; A61M 5/3135; A61M 2005/3139; A61M 5/178; A61M 5/315; A61M 5/3129; A61M 5/00
See application file for complete search history.

(56) References Cited

U.S. PATENT DOCUMENTS

| | | | |
|---|---|---|---|
| 1,250,114 | A | 12/1917 | Bigelow et al. |
| 1,558,037 | A | 10/1925 | Morton |
| 1,591,021 | A | 7/1926 | Davis |

(Continued)

FOREIGN PATENT DOCUMENTS

| | | |
|---|---|---|
| CN | 2535071 | 2/2003 |
| CN | 1638827 | 7/2005 |

(Continued)

OTHER PUBLICATIONS

Bleyer, Mark, SIS Facial Implant 510(k) Summary, Cook Biotech, Inc., May 19, 2005.

(Continued)

*Primary Examiner* — Nathan R Price
*Assistant Examiner* — Mark A Igel
(74) *Attorney, Agent, or Firm* — Mintz, Levin, Cohn, Ferris, Glovsky and Popeo, P.C.

(57) ABSTRACT

An aspiration and injection device is provided that can allow for ergonomic, safe, and precise aspiration of a target site and ejection of a medicament to the target site. The device can include a syringe barrel, a flange extender couplable to the barrel, and plunger that can be engaged by a hand and/or one or more finger of a user to perform aspiration and injection at a target site.

10 Claims, 6 Drawing Sheets

(56) References Cited

U.S. PATENT DOCUMENTS

| | | | |
|---|---|---|---|
| 2,007,140 A | 7/1935 | Ragnar | |
| 2,092,427 A | 9/1937 | Frederick | |
| 2,302,986 A | 11/1942 | Vollrath | |
| 2,491,978 A | 12/1949 | Heitman | |
| 2,551,902 A | 5/1951 | Rieck | |
| 2,571,653 A | 10/1951 | Victor | |
| 2,737,946 A | 3/1956 | Hein, Jr. | |
| 2,826,195 A * | 3/1958 | Ashkenaz | A61M 5/24 |
| | | | 604/193 |
| 2,830,586 A * | 4/1958 | Dann | A61M 5/28 |
| | | | D24/114 |
| 2,842,128 A * | 7/1958 | Hein, Jr. | A61M 5/315 |
| | | | 604/227 |
| 2,853,070 A | 9/1958 | Julliard | |
| 2,972,991 A * | 2/1961 | Burke | A61M 5/178 |
| | | | 604/110 |
| 3,028,862 A * | 4/1962 | Prater, Jr. | A61M 5/31511 |
| | | | D24/114 |
| 3,086,530 A | 4/1963 | Groom | |
| 3,135,260 A * | 6/1964 | Hamilton | A61M 5/31513 |
| | | | 604/222 |
| 3,161,323 A | 12/1964 | Bent | |
| 3,204,635 A | 9/1965 | Voss | |
| D202,754 S | 11/1965 | Fnftolin | |
| D214,112 S | 5/1969 | Langdon | |
| 3,517,668 A | 6/1970 | Brickson | |
| 3,572,337 A * | 3/1971 | Schunk | A61J 7/0053 |
| | | | D24/114 |
| 3,595,231 A | 7/1971 | Pistor | |
| D224,066 S | 6/1972 | McDonald | |
| 3,674,026 A | 7/1972 | Werner | |
| 3,720,211 A | 3/1973 | Kyrias | |
| 3,767,085 A | 10/1973 | Cannon et al. | |
| 3,807,048 A | 4/1974 | Malmin | |
| 3,910,282 A | 10/1975 | Messer et al. | |
| 3,916,777 A | 11/1975 | Earl | |
| 3,943,926 A * | 3/1976 | Arvizu Barragan | A61M 5/24 |
| | | | 604/227 |
| 4,064,879 A | 12/1977 | Leibinsohn | |
| 4,135,508 A * | 1/1979 | Lyons | E04F 11/025 |
| | | | 182/194 |
| 4,240,423 A | 12/1980 | Akhavi | |
| 4,240,426 A | 12/1980 | Akhavi | |
| 4,273,122 A | 6/1981 | Whitney et al. | |
| 4,324,241 A * | 4/1982 | Reese | A61M 5/31 |
| | | | 604/227 |
| 4,326,517 A | 4/1982 | Whitney et al. | |
| 4,346,708 A | 8/1982 | Leveen | |
| 4,351,334 A * | 9/1982 | Inglefield, Jr. | A61M 5/3148 |
| | | | 604/227 |
| 4,402,308 A | 9/1983 | Scott | |
| 4,444,560 A | 4/1984 | Jacklich | |
| 4,451,253 A | 5/1984 | Harman | |
| 4,529,401 A | 7/1985 | Leslie et al. | |
| 4,605,691 A | 8/1986 | Balazs | |
| 4,617,016 A | 10/1986 | Blomberg | |
| 4,624,659 A | 11/1986 | Goldberg | |
| 4,627,444 A | 12/1986 | Brooker | |
| 4,671,255 A | 6/1987 | Dubrul et al. | |
| 4,695,273 A | 9/1987 | Brown | |
| 4,699,612 A | 10/1987 | Hamacher | |
| 4,710,172 A | 12/1987 | Jacklich | |
| 4,719,918 A | 1/1988 | Bonomo et al. | |
| 4,755,169 A | 7/1988 | Sarnoff | |
| 4,759,750 A | 7/1988 | Devries | |
| 4,767,413 A * | 8/1988 | Haber | A61M 5/326 |
| | | | 604/232 |
| 4,800,901 A | 1/1989 | Rosenberg | |
| 4,820,267 A | 4/1989 | Harman | |
| 4,832,692 A | 5/1989 | Box | |
| 4,841,948 A | 6/1989 | Bauer et al. | |
| 4,841,992 A | 6/1989 | Sasaki et al. | |
| 4,846,886 A | 7/1989 | Fey et al. | |
| D303,010 S | 8/1989 | Jabbusch | |
| 4,869,717 A | 9/1989 | Adair | |
| 4,898,572 A | 2/1990 | Surugue nee Lasnier | |
| 4,908,029 A | 3/1990 | Bark et al. | |
| 4,909,932 A | 3/1990 | Monnet | |
| 4,955,905 A | 9/1990 | Reed | |
| 4,957,744 A | 9/1990 | della Valle et al. | |
| 4,994,028 A | 2/1991 | Leonard | |
| 5,019,053 A * | 5/1991 | Hoffman | A61M 5/315 |
| | | | 604/220 |
| 5,024,613 A | 6/1991 | Vasconcellos | |
| 5,024,656 A | 6/1991 | Gasaway et al. | |
| 5,046,506 A | 9/1991 | Singer | |
| 5,066,303 A | 11/1991 | Bark et al. | |
| 5,092,348 A | 3/1992 | Dubrul et al. | |
| 5,100,390 A | 3/1992 | Lubeck et al. | |
| 5,104,375 A | 4/1992 | Wolf et al. | |
| 5,116,358 A | 5/1992 | Granger et al. | |
| 5,127,436 A | 7/1992 | Campion et al. | |
| 5,135,511 A * | 8/1992 | Houghton | A61M 5/3148 |
| | | | 604/233 |
| 5,137,181 A | 8/1992 | Keller | |
| 5,141,496 A | 8/1992 | Dalto et al. | |
| 5,211,644 A | 5/1993 | VanBeek et al. | |
| 5,215,535 A | 6/1993 | Gettig | |
| 5,222,942 A * | 6/1993 | Bader | A61B 5/150236 |
| | | | 604/218 |
| 5,254,105 A | 10/1993 | Haaga | |
| 5,258,013 A | 11/1993 | Granger et al. | |
| 5,270,685 A | 12/1993 | Hagen | |
| 5,275,582 A * | 1/1994 | Wimmer | A61M 5/31513 |
| | | | 604/218 |
| 5,279,544 A | 1/1994 | Gross | |
| 5,295,980 A | 3/1994 | Ersek | |
| 5,304,119 A | 4/1994 | Balaban | |
| 5,305,788 A | 4/1994 | Mayeux | |
| 5,318,544 A | 6/1994 | Drypen | |
| 5,322,511 A | 6/1994 | Armbruster et al. | |
| 5,344,407 A | 9/1994 | Ryan | |
| 5,350,385 A | 9/1994 | Christy | |
| 5,354,279 A | 10/1994 | Honing | |
| 5,366,447 A | 11/1994 | Gurley | |
| 5,368,572 A | 11/1994 | Shirota | |
| 5,383,851 A | 1/1995 | MacKinnon, Jr. | |
| 5,405,330 A | 4/1995 | Zunitch et al. | |
| 5,433,352 A | 7/1995 | Ronvig | |
| 5,478,327 A | 12/1995 | McGregor et al. | |
| 5,496,286 A * | 3/1996 | Stiehl | A61M 5/24 |
| | | | 604/232 |
| 5,509,903 A * | 4/1996 | Grendahl | A61M 5/178 |
| | | | D24/114 |
| 5,520,658 A | 5/1996 | Holm | |
| 5,540,657 A | 7/1996 | Kurjan | |
| 5,549,672 A | 8/1996 | Maddock et al. | |
| 5,554,133 A * | 9/1996 | Haffner | A61M 5/3135 |
| | | | 604/227 |
| 5,584,815 A | 12/1996 | Pawelka et al. | |
| 5,599,293 A | 2/1997 | Orenga | |
| 5,607,399 A * | 3/1997 | Grimard | A61M 5/315 |
| | | | 604/220 |
| 5,611,809 A | 3/1997 | Marshall et al. | |
| D378,939 S | 4/1997 | Smith et al. | |
| 5,650,317 A | 7/1997 | Chang et al. | |
| 5,667,495 A * | 9/1997 | Bitdinger | A61M 5/315 |
| | | | 604/220 |
| 5,690,618 A | 11/1997 | Smith et al. | |
| 5,716,404 A | 2/1998 | Vacanti | |
| 5,722,829 A | 3/1998 | Wilcox et al. | |
| 5,728,077 A | 3/1998 | Williams | |
| 5,735,827 A | 4/1998 | Adwers | |
| 5,752,970 A | 5/1998 | Yoon | |
| D397,790 S * | 9/1998 | Naganuma | D24/127 |
| 5,803,918 A * | 9/1998 | Vetter | A61M 5/315 |
| | | | 604/110 |
| 5,807,340 A | 9/1998 | Pokras | |
| 5,814,511 A | 9/1998 | Chang et al. | |
| 5,817,033 A | 10/1998 | DeSantis | |
| 5,824,335 A | 10/1998 | Dorigatti et al. | |

(56) References Cited

U.S. PATENT DOCUMENTS

| | | | |
|---|---|---|---|
| 5,833,669 A * | 11/1998 | Wyrick | A61M 5/31595 604/234 |
| 5,846,225 A | 12/1998 | Rosengart et al. | |
| 5,853,388 A | 12/1998 | Semel | |
| 5,897,532 A | 4/1999 | Spallek et al. | |
| 5,941,845 A | 8/1999 | Tu et al. | |
| 5,964,737 A | 10/1999 | Caizza | |
| 5,972,385 A | 10/1999 | Liu et al. | |
| 5,997,513 A | 12/1999 | Smith et al. | |
| 5,997,514 A * | 12/1999 | Balestracci | A61M 5/3135 604/227 |
| 6,004,299 A * | 12/1999 | Arai | A61M 5/347 604/199 |
| D419,671 S * | 1/2000 | Jansen | D24/112 |
| 6,047,861 A | 4/2000 | Vidal et al. | |
| D424,194 S | 5/2000 | Holdaway et al. | |
| 6,077,251 A | 6/2000 | Ting et al. | |
| 6,082,364 A | 7/2000 | Balian et al. | |
| 6,083,912 A | 7/2000 | Khouri | |
| 6,102,920 A | 8/2000 | Sullivan | |
| 6,102,929 A | 8/2000 | Conway et al. | |
| 6,126,644 A * | 10/2000 | Naganuma | A61F 9/007 604/232 |
| 6,129,761 A | 10/2000 | Hubbell et al. | |
| 6,159,233 A | 12/2000 | Matsuzawa | |
| 6,162,203 A | 12/2000 | Haaga | |
| 6,171,276 B1 | 1/2001 | Lippe | |
| 6,171,610 B1 | 1/2001 | Vacanti et al. | |
| 6,176,396 B1 | 1/2001 | Hamada et al. | |
| 6,183,434 B1 | 2/2001 | Eppstein | |
| D441,077 S | 4/2001 | Garito et al. | |
| 6,214,030 B1 | 4/2001 | Matsutani et al. | |
| 6,214,045 B1 | 4/2001 | Corbitt, Jr. et al. | |
| 6,231,552 B1 | 5/2001 | Jentzen | |
| 6,231,570 B1 | 5/2001 | Tu et al. | |
| 6,239,105 B1 | 5/2001 | Brewitt et al. | |
| 6,283,951 B1 | 9/2001 | Flaherty et al. | |
| 6,293,925 B1 | 9/2001 | Safabash et al. | |
| 6,303,518 B1 | 10/2001 | Aceti | |
| 6,312,412 B1 | 11/2001 | Saied | |
| 6,316,247 B1 | 11/2001 | Katz | |
| 6,432,046 B1 | 8/2002 | Yarush et al. | |
| 6,450,937 B1 | 9/2002 | Mercereau | |
| 6,451,240 B1 | 9/2002 | Sherman et al. | |
| 6,482,187 B1 | 11/2002 | Gibbs | |
| 6,488,651 B1 | 12/2002 | Morris | |
| 6,547,762 B1 | 4/2003 | Botich | |
| 6,551,290 B1 | 4/2003 | Elsberry et al. | |
| 6,582,960 B1 | 6/2003 | Martin et al. | |
| 6,595,960 B2 | 7/2003 | West et al. | |
| 6,607,512 B2 | 8/2003 | Oliver | |
| 6,607,513 B1 | 8/2003 | Down | |
| 6,610,033 B1 | 8/2003 | Melanson et al. | |
| 6,611,707 B1 | 8/2003 | Prausnitz et al. | |
| 6,613,010 B2 | 9/2003 | Castellano | |
| 6,616,448 B2 | 9/2003 | Friedman | |
| 6,638,308 B2 | 10/2003 | Corbitt | |
| D483,116 S | 12/2003 | Castellano | |
| 6,656,488 B2 | 12/2003 | Yi et al. | |
| 6,666,893 B2 | 12/2003 | Burg et al. | |
| 6,689,095 B1 | 2/2004 | Garitano et al. | |
| 6,689,103 B1 | 2/2004 | Palasis | |
| 6,777,231 B1 | 8/2004 | Katz et al. | |
| 6,780,171 B2 | 8/2004 | Gabel | |
| 6,783,514 B2 | 8/2004 | Tovey et al. | |
| 6,824,526 B2 | 11/2004 | Castellano | |
| 6,881,226 B2 | 4/2005 | Corbitt | |
| 6,896,666 B2 | 5/2005 | Kochamba | |
| 6,901,850 B2 | 6/2005 | Corominas | |
| 6,908,453 B2 | 6/2005 | Fleming | |
| 6,916,603 B2 | 7/2005 | Baron et al. | |
| 6,936,297 B2 | 8/2005 | Roby et al. | |
| 6,945,952 B2 | 9/2005 | Kwon | |
| 6,991,652 B1 | 1/2006 | Burg et al. | |
| 7,004,928 B2 | 2/2006 | Aceti | |
| 7,015,037 B1 | 3/2006 | Furcht et al. | |
| 7,018,356 B2 | 3/2006 | Wise et al. | |
| 7,033,337 B2 | 4/2006 | Hjertman | |
| 7,041,088 B2 | 5/2006 | Nawrocki et al. | |
| 7,047,070 B2 | 5/2006 | Wilkinson et al. | |
| 7,048,729 B2 | 5/2006 | Meglin et al. | |
| 7,097,631 B2 | 8/2006 | Trautman | |
| 7,108,681 B2 | 9/2006 | Gartstein | |
| 7,115,108 B2 | 10/2006 | Wilkinson et al. | |
| 7,129,209 B2 | 10/2006 | Rhee et al. | |
| 7,150,726 B2 | 12/2006 | Dalton | |
| 7,285,266 B2 | 10/2007 | Vournakis et al. | |
| 7,302,885 B2 | 12/2007 | Townsend | |
| 7,316,822 B2 | 1/2008 | Binette et al. | |
| 7,361,163 B2 | 4/2008 | Cohen | |
| 7,390,313 B2 * | 6/2008 | Bonacci | A61M 5/007 604/151 |
| 7,390,484 B2 | 6/2008 | Fraser | |
| 7,419,472 B2 | 9/2008 | Hibner et al. | |
| 7,442,187 B2 | 10/2008 | Khayal et al. | |
| D581,527 S * | 11/2008 | Jansen | D24/130 |
| 7,445,793 B2 | 11/2008 | Niwa et al. | |
| 7,488,307 B2 * | 2/2009 | Rimlinger | A61M 5/3202 604/110 |
| 7,494,473 B2 | 2/2009 | Eggers et al. | |
| 7,501,115 B2 | 3/2009 | Fraser et al. | |
| 7,504,386 B2 | 3/2009 | Pressato et al. | |
| 7,514,075 B2 | 4/2009 | Hedrick et al. | |
| 7,556,615 B2 | 7/2009 | Pettis et al. | |
| 7,559,952 B2 | 7/2009 | Pinchuk | |
| 7,560,276 B2 | 7/2009 | Harmon et al. | |
| 7,588,547 B2 | 9/2009 | Deem | |
| 7,611,495 B1 | 11/2009 | Gianturco | |
| 7,651,475 B2 | 1/2010 | Angel | |
| 7,651,684 B2 | 1/2010 | Hedrick et al. | |
| 7,662,110 B2 | 2/2010 | Flaherty | |
| 7,664,545 B2 | 2/2010 | Westersten et al. | |
| 7,666,339 B2 | 2/2010 | Chaouk et al. | |
| D615,192 S | 5/2010 | Mudd et al. | |
| 7,722,582 B2 | 5/2010 | Lina et al. | |
| 7,762,983 B2 | 7/2010 | Arnissolle | |
| 7,767,452 B2 | 8/2010 | Kleinsek et al. | |
| 7,799,767 B2 | 9/2010 | Lamberti et al. | |
| 7,850,656 B2 | 12/2010 | McKay et al. | |
| 7,850,683 B2 | 12/2010 | Elkins | |
| 7,875,296 B2 | 1/2011 | Binette et al. | |
| 7,878,981 B2 | 2/2011 | Strother et al. | |
| 7,896,837 B2 | 3/2011 | Wilkinson et al. | |
| D637,287 S | 5/2011 | Mudd et al. | |
| 7,998,170 B2 | 8/2011 | Cunningham | |
| 8,012,139 B2 | 9/2011 | McKay et al. | |
| 8,029,460 B2 | 10/2011 | Rush et al. | |
| 8,053,423 B2 | 11/2011 | Lamberti et al. | |
| 8,066,629 B2 | 11/2011 | Dlugos | |
| 8,066,691 B2 | 11/2011 | Khouri | |
| 8,083,722 B2 | 12/2011 | McKay et al. | |
| 8,088,108 B2 | 1/2012 | Kraft | |
| 8,137,705 B2 | 3/2012 | Doyle et al. | |
| 8,153,591 B2 | 4/2012 | Masters et al. | |
| 8,157,830 B2 | 4/2012 | Wenchell | |
| 8,172,815 B2 | 5/2012 | Down et al. | |
| 8,177,792 B2 | 5/2012 | Lubock | |
| 8,216,190 B2 | 7/2012 | Gartstein | |
| 8,236,021 B2 | 8/2012 | Kluge | |
| 8,291,768 B2 | 10/2012 | Spiegel | |
| 8,303,518 B2 | 11/2012 | Aceti | |
| 8,303,545 B2 | 11/2012 | Schraga | |
| 8,343,132 B2 | 1/2013 | Heneveld et al. | |
| 8,349,554 B2 | 1/2013 | Bahrami et al. | |
| 8,353,871 B2 | 1/2013 | Zimmerman | |
| 8,366,643 B2 | 2/2013 | Deem | |
| 8,394,118 B2 | 3/2013 | Jones et al. | |
| 8,409,147 B2 | 4/2013 | Kraft | |
| 8,409,185 B2 | 4/2013 | Burger | |
| 8,480,630 B2 | 7/2013 | Mudd et al. | |
| 8,535,278 B2 | 9/2013 | Mudd et al. | |
| 8,556,495 B2 * | 10/2013 | Axen | A61M 5/31596 366/189 |
| 8,562,571 B2 | 10/2013 | Mudd et al. | |

(56) References Cited

U.S. PATENT DOCUMENTS

| | | | |
|---|---|---|---|
| 8,603,028 B2 | 12/2013 | Mudd et al. | |
| 8,628,495 B2 * | 1/2014 | Horton | A61M 5/14546 |
| | | | 604/233 |
| 8,632,501 B2 | 1/2014 | Kraft | |
| 8,636,797 B2 | 1/2014 | Chitre et al. | |
| 8,652,216 B2 | 2/2014 | Chen | |
| 8,657,786 B2 | 2/2014 | Bahrami et al. | |
| 8,668,675 B2 | 3/2014 | Chase | |
| 8,708,965 B2 | 4/2014 | Boyden | |
| 8,712,815 B1 | 4/2014 | Nichols et al. | |
| 8,821,446 B2 | 9/2014 | Trautman | |
| 8,900,181 B2 | 12/2014 | Knowlton | |
| 8,900,186 B2 | 12/2014 | Pettis et al. | |
| 8,945,060 B2 | 2/2015 | Bunch | |
| 9,017,289 B2 | 4/2015 | Backes | |
| 9,017,318 B2 | 4/2015 | Fourkas | |
| 9,039,688 B2 | 5/2015 | Palmer, III | |
| 9,066,712 B2 | 6/2015 | Fourkas | |
| 9,072,498 B2 | 7/2015 | Elkins | |
| 9,101,346 B2 | 8/2015 | Burger | |
| 9,113,855 B2 | 8/2015 | Burger | |
| 9,149,331 B2 | 10/2015 | Deem | |
| 9,155,584 B2 | 10/2015 | Fourkas | |
| 9,180,273 B2 | 11/2015 | Konstantino | |
| 9,227,023 B2 | 1/2016 | Kraft | |
| 9,241,753 B2 | 1/2016 | Fourkas | |
| 9,254,162 B2 | 2/2016 | Burger | |
| 9,289,605 B2 | 3/2016 | Choi | |
| 9,314,568 B2 | 4/2016 | Gurtner et al. | |
| 9,468,748 B2 | 10/2016 | Bang | |
| D790,691 S * | 6/2017 | Davis | D24/130 |
| 9,801,688 B2 | 10/2017 | Jones | |
| D812,223 S * | 3/2018 | Evans | D24/130 |
| 10,086,149 B2 * | 10/2018 | Dugand | A61M 5/3245 |
| D842,463 S * | 3/2019 | Grunhut | D24/130 |
| D845,476 S * | 4/2019 | Evans | D24/130 |
| 10,258,502 B2 * | 4/2019 | Tsai | A61M 5/2053 |
| 10,357,615 B2 * | 7/2019 | Franklin | A61M 5/31556 |
| 10,799,639 B2 * | 10/2020 | Wei | A61M 5/3129 |
| 11,298,462 B2 * | 4/2022 | Atterbury | A61M 5/3148 |
| 2001/0008937 A1 | 7/2001 | Callegaro et al. | |
| 2001/0050084 A1 | 12/2001 | Knudson | |
| 2002/0010433 A1 | 1/2002 | Johnson | |
| 2002/0026039 A1 | 2/2002 | Bellini et al. | |
| 2002/0065483 A1 | 5/2002 | Leon | |
| 2002/0133114 A1 | 9/2002 | Itoh | |
| 2002/0151843 A1 | 10/2002 | Correa et al. | |
| 2003/0023250 A1 | 1/2003 | Watschke | |
| 2003/0028154 A1 | 2/2003 | Ros | |
| 2003/0035744 A1 * | 2/2003 | Horita | A61M 5/31511 |
| | | | 417/469 |
| 2003/0050602 A1 | 3/2003 | Pettis et al. | |
| 2003/0078912 A1 | 4/2003 | Oliver | |
| 2003/0097079 A1 | 5/2003 | Garcia | |
| 2003/0109769 A1 | 6/2003 | Lowery | |
| 2003/0144632 A1 | 7/2003 | Hommann et al. | |
| 2003/0181863 A1 | 9/2003 | Ackley | |
| 2003/0199883 A1 | 10/2003 | Laks | |
| 2003/0220615 A1 * | 11/2003 | Fabian | A61M 5/3137 |
| | | | 604/227 |
| 2003/0233067 A1 | 12/2003 | McIntosh et al. | |
| 2004/0010224 A1 | 1/2004 | Bodmeier | |
| 2004/0015133 A1 | 1/2004 | Karim | |
| 2004/0034323 A1 * | 2/2004 | Manthey | A61M 5/3243 |
| | | | 604/198 |
| 2004/0092011 A1 | 5/2004 | Wilkison et al. | |
| 2004/0092927 A1 | 5/2004 | Podhajsky et al. | |
| 2004/0116893 A1 * | 6/2004 | Spohn | A61M 5/14546 |
| | | | 604/181 |
| 2004/0147883 A1 | 7/2004 | Tsai | |
| 2004/0192643 A1 | 9/2004 | Pressato et al. | |
| 2004/0215133 A1 * | 10/2004 | Weber | A61B 17/3468 |
| | | | 604/60 |
| 2004/0220532 A1 | 11/2004 | Caizza | |
| 2004/0254539 A1 * | 12/2004 | Wolbring | A61M 5/3135 |
| | | | 604/187 |
| 2005/0025755 A1 | 2/2005 | Hedrick | |
| 2005/0033362 A1 | 2/2005 | Grafton | |
| 2005/0075606 A1 | 4/2005 | Botich | |
| 2005/0085767 A1 | 4/2005 | Menassa | |
| 2005/0101917 A1 * | 5/2005 | Doyle | A61M 5/326 |
| | | | 604/187 |
| 2005/0123895 A1 | 6/2005 | Freund | |
| 2005/0131353 A1 | 6/2005 | Mossanen-Shams et al. | |
| 2005/0137496 A1 | 6/2005 | Walsh et al. | |
| 2005/0147562 A1 | 7/2005 | Hunter et al. | |
| 2005/0154399 A1 * | 7/2005 | Weber | A61F 9/0017 |
| | | | 606/107 |
| 2005/0177117 A1 | 8/2005 | Crocker et al. | |
| 2005/0182446 A1 | 8/2005 | DeSantis | |
| 2005/0203542 A1 * | 9/2005 | Weber | A61F 2/167 |
| | | | 606/107 |
| 2005/0215956 A1 | 9/2005 | Nerney | |
| 2005/0261633 A1 | 11/2005 | Khalaj | |
| 2005/0288625 A1 * | 12/2005 | Rossback | A61M 5/2053 |
| | | | 604/93.01 |
| 2006/0041320 A1 | 2/2006 | Matsuda | |
| 2006/0079765 A1 | 4/2006 | Neer | |
| 2006/0089594 A1 | 4/2006 | Landau | |
| 2006/0136070 A1 | 6/2006 | Pinchuk | |
| 2006/0150742 A1 | 7/2006 | Esnouf | |
| 2006/0161114 A1 * | 7/2006 | Perot | A61F 9/0017 |
| | | | 604/198 |
| 2006/0270998 A1 * | 11/2006 | Marti | A61M 5/425 |
| | | | 604/198 |
| 2007/0038181 A1 | 2/2007 | Melamud | |
| 2007/0083155 A1 | 4/2007 | Muller | |
| 2007/0083164 A1 * | 4/2007 | Barrelle | A61M 5/1782 |
| | | | 604/82 |
| 2007/0085767 A1 | 4/2007 | Jung et al. | |
| 2007/0088284 A1 * | 4/2007 | Witowski | A61M 5/3135 |
| | | | 604/187 |
| 2007/0100363 A1 | 5/2007 | Dollar et al. | |
| 2007/0167920 A1 | 7/2007 | Hommann | |
| 2007/0191781 A1 | 8/2007 | Richards et al. | |
| 2007/0212385 A1 | 9/2007 | David | |
| 2007/0250010 A1 | 10/2007 | Hohlfelder et al. | |
| 2007/0251531 A1 | 11/2007 | Khouri | |
| 2007/0270710 A1 | 11/2007 | Frass et al. | |
| 2008/0015522 A1 | 1/2008 | Yeshurun | |
| 2008/0033347 A1 | 2/2008 | D'Arrigo et al. | |
| 2008/0058706 A1 | 3/2008 | Zhang | |
| 2008/0058839 A1 | 3/2008 | Nobles | |
| 2008/0071385 A1 | 3/2008 | Binette et al. | |
| 2008/0097325 A1 | 4/2008 | Tanaka et al. | |
| 2008/0108952 A1 | 5/2008 | Horvath et al. | |
| 2008/0114305 A1 | 5/2008 | Gerondale | |
| 2008/0119797 A1 | 5/2008 | Kim | |
| 2008/0119876 A1 | 5/2008 | Price et al. | |
| 2008/0125766 A1 | 5/2008 | Lubock | |
| 2008/0139928 A1 | 6/2008 | Lubock | |
| 2008/0161772 A1 | 7/2008 | Nayak | |
| 2008/0167674 A1 | 7/2008 | Bodduluri et al. | |
| 2008/0188816 A1 | 8/2008 | Shimazaki | |
| 2008/0200758 A1 | 8/2008 | Orbay et al. | |
| 2008/0243028 A1 | 10/2008 | Howard et al. | |
| 2008/0281278 A1 | 11/2008 | Williams | |
| 2008/0299213 A2 | 12/2008 | Kleinsek | |
| 2008/0317718 A1 | 12/2008 | Yoshimura | |
| 2009/0088703 A1 | 4/2009 | Azar | |
| 2009/0098177 A1 | 4/2009 | Werkmeister et al. | |
| 2009/0123547 A1 | 5/2009 | Hill | |
| 2009/0124552 A1 | 5/2009 | Hill | |
| 2009/0124996 A1 | 5/2009 | Heneveld et al. | |
| 2009/0125050 A1 | 5/2009 | Dixon | |
| 2009/0131886 A1 | 5/2009 | Liu et al. | |
| 2009/0131908 A1 | 5/2009 | McKay | |
| 2009/0143746 A1 | 6/2009 | Mudd et al. | |
| 2009/0162415 A1 | 6/2009 | Huang et al. | |
| 2009/0182284 A1 * | 7/2009 | Morgan | A61M 5/3202 |
| | | | 604/227 |
| 2009/0187118 A1 | 7/2009 | Kim | |

(56) References Cited

U.S. PATENT DOCUMENTS

| | | |
|---|---|---|
| 2009/0209804 A1 | 8/2009 | Seller |
| 2009/0234322 A1 | 9/2009 | Fischer |
| 2009/0240200 A1 | 9/2009 | Heneveld et al. |
| 2009/0246182 A1 | 10/2009 | Casteilla |
| 2009/0247953 A1 | 10/2009 | Yeshurun |
| 2009/0259180 A1 | 10/2009 | Choi |
| 2009/0275917 A1 | 11/2009 | Azar |
| 2009/0287161 A1 | 11/2009 | Traub |
| 2009/0299328 A1 | 12/2009 | Mudd et al. |
| 2009/0312746 A1 | 12/2009 | Khouri |
| 2009/0317367 A1 | 12/2009 | Chazenbalk |
| 2009/0318875 A1 | 12/2009 | Friedman |
| 2010/0006095 A1 | 1/2010 | Woodcock |
| 2010/0010627 A1 | 1/2010 | Matheny |
| 2010/0030152 A1 | 2/2010 | Lee et al. |
| 2010/0069848 A1 | 3/2010 | Alferness |
| 2010/0100114 A1 | 4/2010 | Berger |
| 2010/0121307 A1 | 5/2010 | Lockard |
| 2010/0152675 A1 | 6/2010 | McClintock |
| 2010/0152679 A1 | 6/2010 | Tezel |
| 2010/0179488 A1 | 7/2010 | Spiegel |
| 2010/0185205 A1* | 7/2010 | Novakovic ............ A61F 2/167 606/107 |
| 2010/0256594 A1 | 10/2010 | Kimmell |
| 2010/0256596 A1 | 10/2010 | Chomas |
| 2010/0279405 A1 | 11/2010 | Peterson |
| 2010/0280488 A1 | 11/2010 | Pruiitt et al. |
| 2010/0282774 A1 | 11/2010 | Greter et al. |
| 2010/0286618 A1 | 11/2010 | Choi |
| 2011/0009808 A1 | 1/2011 | AlGhamdi |
| 2011/0021905 A1 | 1/2011 | Patrick et al. |
| 2011/0028910 A1 | 2/2011 | Weber |
| 2011/0070281 A1 | 3/2011 | Altman et al. |
| 2011/0092916 A1 | 4/2011 | Tezel et al. |
| 2011/0093088 A1 | 4/2011 | Chen |
| 2011/0137286 A1 | 6/2011 | Mudd et al. |
| 2011/0150823 A1 | 6/2011 | Huang |
| 2011/0152926 A1 | 6/2011 | Vetrecin |
| 2011/0160674 A1 | 6/2011 | Holmes et al. |
| 2011/0172645 A1 | 7/2011 | Moga |
| 2011/0190974 A1 | 8/2011 | Holmes et al. |
| 2011/0202014 A1 | 8/2011 | Mutzbauer |
| 2011/0213336 A1 | 9/2011 | Cucin |
| 2011/0218494 A1 | 9/2011 | Assaf |
| 2011/0218497 A1 | 9/2011 | Assaf |
| 2011/0230839 A1 | 9/2011 | Bahrami et al. |
| 2011/0238038 A1 | 9/2011 | Sefi |
| 2011/0263724 A1 | 10/2011 | Gurtner et al. |
| 2011/0276026 A1* | 11/2011 | Dowds ............... A61M 5/3213 604/506 |
| 2011/0282324 A1 | 11/2011 | Kurokawa et al. |
| 2011/0282381 A1 | 11/2011 | Cronin et al. |
| 2011/0282447 A1 | 11/2011 | Niu |
| 2011/0319865 A1 | 12/2011 | Buss |
| 2012/0010146 A1 | 1/2012 | Han et al. |
| 2012/0041374 A1 | 2/2012 | Lee |
| 2012/0076868 A1 | 3/2012 | Lamberti et al. |
| 2012/0089211 A1 | 4/2012 | Curtis |
| 2012/0101475 A1 | 4/2012 | Wilmot |
| 2012/0108895 A1 | 5/2012 | Neuman |
| 2012/0109072 A1* | 5/2012 | Tabata .................... A61M 5/28 604/192 |
| 2012/0123194 A1 | 5/2012 | Beckman |
| 2012/0123537 A1 | 5/2012 | Manesis et al. |
| 2012/0141532 A1 | 6/2012 | Blanda et al. |
| 2012/0150266 A1 | 6/2012 | Shalev |
| 2012/0156265 A1 | 6/2012 | Binette et al. |
| 2012/0209248 A1 | 8/2012 | Gurtner et al. |
| 2012/0215230 A1 | 8/2012 | Lubock et al. |
| 2012/0220948 A1* | 8/2012 | Barbour ............... A61M 5/3137 604/218 |
| 2012/0245629 A1 | 9/2012 | Gross et al. |
| 2012/0259322 A1 | 10/2012 | Fourkas |
| 2012/0265064 A1 | 10/2012 | Bahrami et al. |
| 2012/0265171 A1 | 10/2012 | Thorne |
| 2012/0279996 A1* | 11/2012 | Pappalardo ......... A61M 5/2053 222/326 |
| 2012/0289905 A1* | 11/2012 | Julian ................ A61M 5/3137 604/189 |
| 2012/0296206 A1 | 11/2012 | Bahrami et al. |
| 2013/0012865 A1 | 1/2013 | Sallberg et al. |
| 2013/0018325 A1* | 1/2013 | Schiller ............... A61M 5/3137 264/299 |
| 2013/0041346 A1 | 2/2013 | Alon |
| 2013/0096531 A1 | 4/2013 | Estepa et al. |
| 2013/0122068 A1 | 5/2013 | Fermanian et al. |
| 2013/0131632 A1 | 5/2013 | Mudd et al. |
| 2013/0131633 A1 | 5/2013 | Mudd et al. |
| 2013/0150826 A1 | 6/2013 | Almohizea |
| 2013/0178737 A1* | 7/2013 | Anelli ................... A61M 5/007 600/432 |
| 2013/0184648 A1 | 7/2013 | Inou et al. |
| 2013/0184696 A1 | 7/2013 | Fourkas |
| 2013/0197446 A1 | 8/2013 | Gustafsson |
| 2013/0197449 A1 | 8/2013 | Franklin et al. |
| 2013/0211374 A1 | 8/2013 | Hetherington |
| 2013/0226235 A1 | 8/2013 | Fermanian et al. |
| 2013/0253289 A1 | 9/2013 | Hadvary |
| 2013/0274222 A1 | 10/2013 | Horne et al. |
| 2013/0274655 A1 | 10/2013 | Jennings |
| 2013/0274670 A1 | 10/2013 | Mudd et al. |
| 2013/0280755 A1 | 10/2013 | Hubert |
| 2013/0310750 A1 | 11/2013 | Hopman |
| 2013/0310763 A1 | 11/2013 | Mudd et al. |
| 2014/0018770 A1 | 1/2014 | Sutkin |
| 2014/0018835 A1 | 1/2014 | Scherkowski |
| 2014/0066845 A1 | 3/2014 | Mudd et al. |
| 2014/0088502 A1 | 3/2014 | Matheny et al. |
| 2014/0088553 A1 | 3/2014 | Hetherington |
| 2014/0114279 A1 | 4/2014 | Klinghoffer |
| 2014/0121587 A1 | 5/2014 | Sallberg et al. |
| 2014/0128685 A1 | 5/2014 | Na |
| 2014/0128810 A1 | 5/2014 | Ozawa et al. |
| 2014/0162901 A1 | 6/2014 | Bahrami et al. |
| 2014/0170299 A1 | 6/2014 | Gill |
| 2014/0221940 A1 | 8/2014 | Clauson et al. |
| 2014/0228950 A1 | 8/2014 | Whitcup et al. |
| 2014/0228971 A1 | 8/2014 | Kim |
| 2014/0249504 A1 | 9/2014 | Franklin et al. |
| 2014/0257179 A1 | 9/2014 | Schwab et al. |
| 2014/0257190 A1 | 9/2014 | Yue et al. |
| 2014/0276378 A1 | 9/2014 | Chen |
| 2014/0309590 A1 | 10/2014 | Bahrami et al. |
| 2014/0343481 A1 | 11/2014 | Ignon |
| 2014/0350514 A1 | 11/2014 | Levin |
| 2014/0350516 A1 | 11/2014 | Schwab |
| 2014/0350517 A1 | 11/2014 | Dominguez |
| 2014/0350518 A1 | 11/2014 | Franklin et al. |
| 2014/0350536 A1 | 11/2014 | Allison |
| 2015/0025459 A1 | 1/2015 | Kimmell |
| 2015/0025563 A1 | 1/2015 | Mosharrafa et al. |
| 2015/0057608 A1* | 2/2015 | Hitscherich, Jr. ... A61M 5/3137 604/218 |
| 2015/0105734 A1* | 4/2015 | Bryant .................... A61P 43/00 604/218 |
| 2015/0119875 A1 | 4/2015 | Fischell et al. |
| 2015/0126929 A1 | 5/2015 | Franklin et al. |
| 2015/0141956 A1 | 5/2015 | Hoffman et al. |
| 2015/0157809 A1 | 6/2015 | Park et al. |
| 2015/0209265 A1 | 7/2015 | Horne |
| 2015/0209523 A1 | 7/2015 | Horne et al. |
| 2015/0327972 A1 | 11/2015 | Horne et al. |
| 2015/0343147 A1 | 12/2015 | Franklin et al. |
| 2016/0007990 A1 | 1/2016 | Solish et al. |
| 2016/0058488 A1 | 3/2016 | Fourkas |
| 2016/0074307 A1 | 3/2016 | Gurtner et al. |
| 2016/0095984 A1 | 4/2016 | Franklin et al. |
| 2016/0114144 A1 | 4/2016 | Sumida |
| 2016/0144122 A1* | 5/2016 | Locati ............... A61M 5/31501 604/220 |
| 2016/0144125 A1 | 5/2016 | Franklin |
| 2016/0207253 A9 | 7/2016 | Down et al. |
| 2016/0213813 A1 | 7/2016 | Gurtner et al. |
| 2016/0213854 A1 | 7/2016 | Schwab et al. |

(56) References Cited

U.S. PATENT DOCUMENTS

| | | | |
|---|---|---|---|
| 2016/0263358 A1 | 9/2016 | Unger | |
| 2016/0303314 A1 | 10/2016 | Momose | |
| 2017/0028135 A1* | 2/2017 | Fransson | A61M 5/315 |
| 2017/0049972 A1 | 2/2017 | Persons | |
| 2017/0080154 A1 | 3/2017 | Mudd et al. | |
| 2017/0156754 A1 | 6/2017 | Valbuena | |
| 2018/0117256 A1* | 5/2018 | Ruddocks | A61F 9/0017 |
| 2018/0206963 A1 | 7/2018 | Duc et al. | |
| 2018/0206964 A1 | 7/2018 | Duc et al. | |
| 2018/0206965 A1 | 7/2018 | Duc et al. | |
| 2018/0206966 A1 | 7/2018 | Duc et al. | |
| 2018/0206967 A1 | 7/2018 | Duc et al. | |
| 2018/0243509 A1* | 8/2018 | Ohashi | A61M 5/3135 |
| 2019/0328976 A1* | 10/2019 | Evans | A61M 5/3137 |

FOREIGN PATENT DOCUMENTS

| | | | | |
|---|---|---|---|---|
| CN | 200960353 | 10/2007 | | |
| CN | 101232912 | 7/2008 | | |
| CN | 103781504 | 5/2014 | | |
| CN | 204910353 U | 12/2015 | | |
| DE | 19613035 | 9/1997 | | |
| DE | 19613035 A1 * | 9/1997 | | A61M 5/3135 |
| DE | 102005005468 | 8/2006 | | |
| EP | 0167662 | 1/1986 | | |
| EP | 0205915 | 12/1986 | | |
| EP | 0362484 | 4/1990 | | |
| EP | 0648474 | 4/1995 | | |
| EP | 0809968 | 12/1997 | | |
| EP | 0935968 | 8/1999 | | |
| EP | 1051988 | 11/2000 | | |
| EP | 1395320 | 3/2004 | | |
| EP | 1476202 | 11/2004 | | |
| EP | 1486218 | 12/2004 | | |
| EP | 1859827 | 11/2007 | | |
| EP | 1923086 | 5/2008 | | |
| EP | 2103262 | 9/2009 | | |
| EP | 2184016 | 5/2010 | | |
| EP | 2189173 | 5/2010 | | |
| EP | 2298392 | 3/2011 | | |
| EP | 2298392 A1 * | 3/2011 | | A61M 5/001 |
| EP | 2335755 | 6/2011 | | |
| EP | 2422832 | 2/2012 | | |
| EP | 2520318 | 11/2012 | | |
| EP | 2671516 | 12/2013 | | |
| EP | 2873430 | 5/2015 | | |
| EP | 3181168 | 6/2017 | | |
| EP | 3181168 A1 * | 6/2017 | | A61M 5/3135 |
| FR | 53011 | 9/1945 | | |
| FR | 2622457 | 5/1989 | | |
| FR | 2821560 | 9/2002 | | |
| FR | 2821560 A1 * | 9/2002 | | A61M 5/3257 |
| FR | 2830199 | 4/2003 | | |
| FR | 2830199 A1 * | 4/2003 | | A61M 5/3135 |
| FR | 2857654 | 1/2005 | | |
| GB | 2336783 | 11/1999 | | |
| IN | 209387 | 9/2007 | | |
| JP | S49-81393 | 7/1974 | | |
| JP | H 08-294533 | 11/1996 | | |
| JP | H 09-103486 | 4/1997 | | |
| JP | 2008-307241 | 12/2008 | | |
| JP | 2008307241 A * | 12/2008 | | |
| JP | 2015-517860 | 6/2015 | | |
| KR | 20080104258 A * | 12/2008 | | |
| KR | 1020080104258 | 12/2008 | | |
| KR | 1020110089197 | 8/2011 | | |
| KR | 2012-0007473 | 10/2012 | | |
| KR | 101246570 | 3/2013 | | |
| KR | 2013-0036921 | 4/2013 | | |
| KR | 2020130004076 | 7/2013 | | |
| KR | 2013-0130436 | 12/2013 | | |
| KR | 2013-0132196 | 12/2013 | | |
| KR | 2014-0029007 | 3/2014 | | |
| KR | 1020150121632 | 10/2015 | | |
| RU | 2286803 | 11/2006 | | |
| WO | WO 90/01349 | 2/1990 | | |
| WO | WO 92/013579 | 8/1992 | | |
| WO | WO 94/012228 | 6/1994 | | |
| WO | WO 96/025965 | 8/1996 | | |
| WO | WO 97/028840 | 8/1997 | | |
| WO | WO 99/048601 | 9/1999 | | |
| WO | WO 01/00190 | 1/2001 | | |
| WO | WO 02/055135 | 7/2002 | | |
| WO | WO 2004/022603 | 3/2004 | | |
| WO | WO 2005/095225 | 10/2005 | | |
| WO | WO 2006/065837 | 6/2006 | | |
| WO | WO 2006/118804 | 11/2006 | | |
| WO | WO 2006/133111 | 12/2006 | | |
| WO | WO 2007/092929 | 8/2007 | | |
| WO | WO 2007/095922 | 8/2007 | | |
| WO | WO 2007/124478 | 11/2007 | | |
| WO | WO 2008/019265 | 2/2008 | | |
| WO | WO 2008/053481 | 5/2008 | | |
| WO | WO 2008/063569 | 5/2008 | | |
| WO | WO 2008/072229 | 6/2008 | | |
| WO | WO 2008/079824 | 7/2008 | | |
| WO | WO 2008/086479 | 7/2008 | | |
| WO | WO 2008/148026 | 12/2008 | | |
| WO | WO 2008/148071 | 12/2008 | | |
| WO | WO 2009/003135 | 12/2008 | | |
| WO | WO 2009/035680 | 3/2009 | | |
| WO | WO 2009/047346 | 4/2009 | | |
| WO | WO 2009/085548 | 7/2009 | | |
| WO | WO 2009/091099 | 7/2009 | | |
| WO | WO 2009/098666 | 8/2009 | | |
| WO | WO 2009/103818 | 8/2009 | | |
| WO | WO 2009/115581 | 9/2009 | | |
| WO | WO 2009/154107 | 12/2009 | | |
| WO | WO 2009/155583 | 12/2009 | | |
| WO | WO 2009/158145 | 12/2009 | | |
| WO | WO-2009154107 A1 * | 12/2009 | | A61M 5/001 |
| WO | WO 2010/026299 | 3/2010 | | |
| WO | WO 2010/028025 | 3/2010 | | |
| WO | WO 2010/127310 | 11/2010 | | |
| WO | WO 2011/016785 | 2/2011 | | |
| WO | WO 2011/072399 | 6/2011 | | |
| WO | WO 2011/073796 | 6/2011 | | |
| WO | WO 2011/075731 | 6/2011 | | |
| WO | WO 2011/109129 | 9/2011 | | |
| WO | WO 2011/109130 | 9/2011 | | |
| WO | WO 2012/006587 | 1/2012 | | |
| WO | WO 2012/019103 | 2/2012 | | |
| WO | WO 2012/041946 | 4/2012 | | |
| WO | WO 2012/054301 | 4/2012 | | |
| WO | WO 2012/054311 | 4/2012 | | |
| WO | WO 2012/127366 | 9/2012 | | |
| WO | WO 2012/127856 | 9/2012 | | |
| WO | WO 2012/154185 | 11/2012 | | |
| WO | WO-2012154185 A1 * | 11/2012 | | A61M 5/31 |
| WO | WO 2012/172424 | 12/2012 | | |
| WO | WO 2012/174464 | 12/2012 | | |
| WO | WO 2013/005881 | 1/2013 | | |
| WO | WO 2013/054165 | 4/2013 | | |
| WO | WO 2013/055832 | 4/2013 | | |
| WO | WO 2013/065235 | 5/2013 | | |
| WO | WO 2013/082112 | 6/2013 | | |
| WO | WO 2013/106857 | 7/2013 | | |
| WO | WO 2013/178771 | 12/2013 | | |
| WO | WO 2014/025564 | 2/2014 | | |
| WO | WO 2014/026044 | 2/2014 | | |
| WO | WO-2014025564 A1 * | 2/2014 | | A61M 5/178 |
| WO | WO 2014/034032 | 3/2014 | | |
| WO | WO 2014/064536 | 5/2014 | | |
| WO | WO 2014/165868 | 10/2014 | | |
| WO | WO-2014165868 A1 * | 10/2014 | | A61M 5/31595 |
| WO | WO 2014/189161 | 11/2014 | | |
| WO | WO 2015/007243 | 1/2015 | | |
| WO | WO 2015/020982 | 2/2015 | | |
| WO | WO 2015/064031 | 3/2015 | | |
| WO | WO 2015/063507 | 5/2015 | | |
| WO | WO 2015/105269 | 7/2015 | | |
| WO | WO 2015/127339 | 8/2015 | | |
| WO | WO 2015/149031 | 10/2015 | | |
| WO | WO 2016/008845 | 1/2016 | | |

(56) References Cited

FOREIGN PATENT DOCUMENTS

| WO | WO 2016/022865 | 2/2016 |
|----|----------------|--------|
| WO | WO 2016/033584 | 3/2016 |
| WO | WO 2016/033586 | 3/2016 |
| WO | WO 2018/002706 | 1/2018 |
| WO | WO 2018/232408 | 12/2018 |

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968.
Galderma, "Restylane Smart Click System Injection Device," Mar. 2015, retrieved from http://www.red-dot-21.com/products/restylane-smart-click-system-injection-device-22169.
Galderma, "New Restylane Skinboosters SmartClick delivery system wins prestigious Red Dot design award," Jul. 4, 2014, retrieved from http://www.galderma.com/News/articleType/ArticleView/articleId/64/New-Res- tylane-Skinboosters-SmartClick-delivery-system-wins-prestigious-Red-Dot-de- sign-award.
Hamza et al., "A new external filling device in tissue expansion," Plastic and Reconstructive Surgery, Mar. 1998, vol. 101, No. 3, pp. 813-815.
Indian Patent Application No. 190/CHE/2002, filed Mar. 20, 2002, entitled A Subcutaneous Tissue Expander.
Indian Patent Application No. IN2012KO01267 for Tissue Expander, Feb. 8, 2017.
Infusio, "How to Fill a Syringe". Aug. 23, 2011 [Database online] [Retrieved on May 28, 2019] Retrieved from YouTube.com, https://www.youtube.conn/watch?v=Mg5f 4pJFPw.
Kilroy et al., "Cytokine Profile of Human Adipose-Derived Stem Cells: Expression of Angiogenic, Hematopoietic, and Pro-Inflammatory Factors," J. Cell. Physiol., 2007, 702-709.
Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641.
Prime Journal, "Galderma to launch two new syringes at AMWC 2014," Mar. 2014.
Rehman et al., "Secretion of Angiogenic and Antiapoptotic Factors by Human Adipose Stromal Cells," Circulation, 2004, 1292-1298, 109.
Turtlepin, "The Painless Direct Dermal Injector" Product Information, JM Biotech Co Ltd, 2013.
Wang et al., "In vivo stimulation of de novo collagen production caused by cross-linked hyaluronic acid dermal filler injections in photodamaged human skin.", Archives of Dermatology, American Medical Association, US, vol. 143, No. 2, Feb. 1, 2007, pp. 155-163.
Yoshimura et al., "Cell-Assisted Lipotransfer for Cosmetic Breast Augmentation: Supportive Use of Adipose-Derived Stem/Stromal Cells," Aesth. Plast. Surg., 2008, 48-55.
Yoshimura et al., "Cell-Assisted Lipotransfer for Facial Lipoatrophy: Effects of Clinical Use of Adipose-Derived Stem Cells," Dermatol. Surg., 2008, 1178-1185.
Yoshimura et al., "Characterization of Freshly Isolated and Cultured Cells Derived From the Fatty and Fluid Portions of Liposuction Aspirates," J Cell Physiol, 2006, 1011-1041.
International Search Report and Written Opinion from PCT/US2017/024114, dated Jun. 2, 2017, 19 pages.
International Search Report and Written Opinion from PCT/US2009/045831, dated Feb. 24, 2010, 14 pages.
International Search Report and Written Opinion from PCT/US2014/039265, dated Nov. 18, 2014, 18 pages.
International Search Report and Written Opinion from PCT/US2014/039266, dated Aug. 26, 2014, 13 pages.
International Search Report from PCT/US2016/021838, dated May 17, 2016, 3 pages.

\* cited by examiner

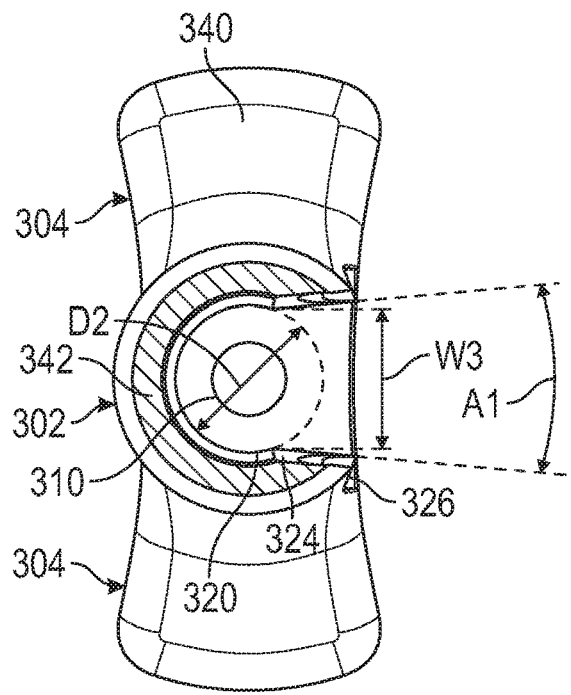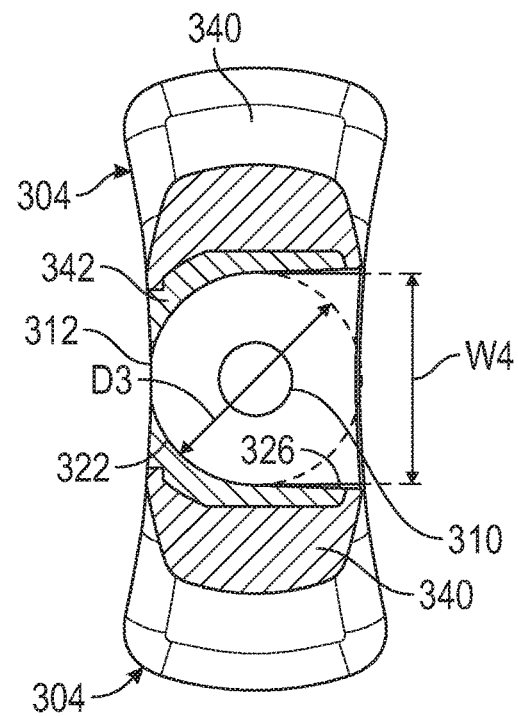
FIG. 7A  FIG. 7B
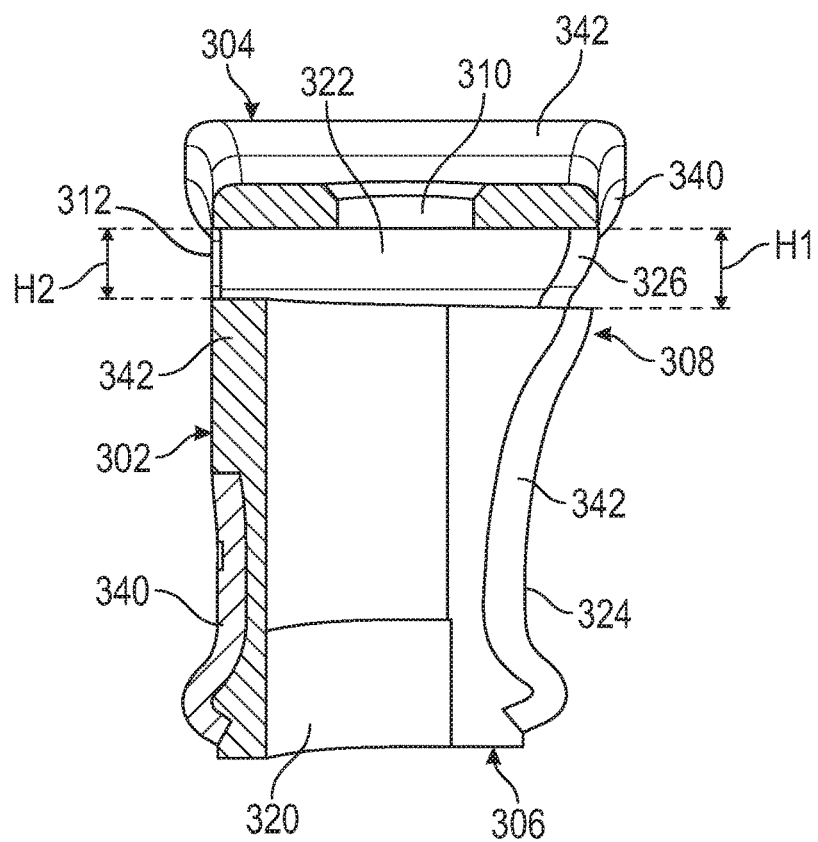
FIG. 8

ASPIRATION AND INJECTION DEVICE

CROSS-REFERENCE TO RELATED APPLICATIONS

This application is a continuation of U.S. application Ser. No. 15/469,004, entitled "ASPIRATION AND INJECTION DEVICE," filed on Mar. 24, 2017, which claims the benefit of U.S. Provisional Application No. 62/320,281, entitled "ASPIRATION AND INJECTION DEVICE," filed Apr. 8, 2016, the disclosure of each of which is incorporated herein by reference in its entirety.

BACKGROUND

Field of the Inventions

The present inventions generally relate to mechanisms for aspiration and injection, and more specifically, to devices for providing ergonomic, safe, and precise aspiration and ejection of a fluid, such as a dermal filler, to a target site.

Description of the Related Art

Aesthetic dermal filler procedures have become increasing popular in recent years, as they have proven to be quite effective in improving the appearance of the face, for example, in reducing the signs of aging by smoothing wrinkles and folds, such as the nasolabial folds, and plumping the midface. Some of the more popular dermal fillers are soft, colorless gel compositions made of hyaluronic acid. Hyaluronic acid (HA) is a long chain polymer, more specifically, a polysaccharide, which occurs naturally in body tissues. When chemically crosslinked, hyaluronic acid makes an excellent, long lasting, dermal filler material. Dermal filler procedures are quite minimally invasive, and the results are nearly immediate. Further, hyaluronic acid naturally degrades in the body tissues, and thus the fillers are temporary, for example, lasting several months to a year or more. Further, results of hyaluronic acid based dermal filler procedures can be reversed using hyaluronidase.

Conventional dermal filler procedures are generally performed by injection of the composition into or below the skin using a standard syringe and a fine gauge needle. A typical dermal filler patient may undergo from about 5 to about 10 injections in a single procedure, with injection points across various regions of the face, neck, decolletage, hands, or other such areas. While the goal may be to improve the appearance of the entire face, a skilled aesthetic physician generally aims to correct one or more specific regions of the face, for example, regions that lack volume such as the lips or the cheeks, or regions that present specific wrinkles, such as deep nasolabial folds, with specific input from the patient regarding areas believed to be detracting to their appearance. Injections are typically for volumetric improvement, sculpting, and/or wrinkle filling. These corrective areas typically represent specific regions (i.e., lips, brow, radial cheek lines, etc.).

Most commercial dermal fillers are considered safe and are physiologically well tolerated. However, if proper precaution is not taken, a rare complication may occur during treatment, which is the introduction of the filler into a blood vessel. It is therefore recommended that physicians, when injecting a dermal filler, first "aspirate" the syringe to ensure the needle tip is not located within a blood vessel, prior to injecting the dermal filler.

Aspiration is typically performed by first inserting the tip of the needle into the skin at the desired injection site and, while using a free hand to hold the syringe and keep the needle position still, using the other hand to retract a syringe plunger. If the physician observes that blood is pulled into the syringe, this indicates that the needle tip may be located in a vessel, and should be removed and repositioned. The physician can then move the needle tip to a different location, and repeat the aspiration procedure. When the physician does not see blood aspirated into the syringe upon withdrawal of the syringe plunger, the physician can then proceed to move the plunger forward direction to safely inject the dermal filler.

It can be appreciated that the aspiration procedure can be cumbersome in that it requires changing of the physician's grip. Although this may not seem to be problematic in itself, anywhere from tens to thousands of injections must be made to treat large surface area, such as the entire face, neck décolletage, hands or other such areas. Further, the treatment procedures may be repeated by a physician multiple times throughout the day. Accordingly, physical and mental fatigue can result, making it difficult to maintain the safety and precision needed during the treatment.

SUMMARY

As noted, HA gel can be used as well to improve overall skin quality of a large surface area, such as the entire face, neck décolletage, hands or other such areas via typical needle injection. To improve skin quality of these surface areas, anywhere from tens to thousands of injections must be made. However, in accordance with at least some embodiments disclosed herein is the realization that it would not be practical or efficient to aspirate each injection site if the physician must change their grip on syringe before each injection, especially when tens, hundreds, or thousands of injections are performed. This can be difficult for both the patient and the physician.

Accordingly, in some embodiments, an aspiration and injection device is provided that can allow for ergonomic, safe, and precise aspiration and injection at a target site by a physician. In some embodiments, the present disclosure permits aspiration and injection at a target site using a single hand. Optionally, some embodiments of the device can be used with a syringe that comprises one or multiple needles.

The device or procedure can be faster than otherwise possible compared to procedures using a standard needle and syringe. Additionally, the device can work with existing gel packaging techniques, such as standard sized syringes. These and various other advantages, some of which are disclosed herein, are made possible by the various embodiments of the syringe system disclosed herein.

For example, in some embodiments, a plunger for a syringe can comprise a plunger rod and a plunger head that has engagement structures extending from a surface of the plunger head. The engagement structures can extend from any of a proximal-facing surface, distal-facing surface, and a side surface of the plunger. The engagement structures can be used to facilitate gripping with a user's thumb during operation of the syringe. The engagement structures can be used to move the plunger relative to the barrel. The engagement structures can be engaged to move the plunger into an inner lumen of the barrel and/or out of the inner lumen of the barrel.

Optionally, in some embodiments, the present disclosure provides a flange extender for a syringe. The flange extender can comprise a central body having grip members extending from the central body. The flange extender can work with an existing syringe or can be formed with a syringe. In some embodiments, the flange extender can be removably coupled with a syringe.

The flange extender can have any of a longitudinal bore and an engagement slot to receive the syringe or a portion of the syringe. The flange extender can be coupled with a syringe by inserting a barrel and a flange of the syringe through the engagement slot and into the longitudinal bore.

The flange extender can be used to facilitate gripping and handling of the system by the physician using one or more fingers and/or hand(s) during operation of the syringe. The flange extender can be used to hold the barrel of the syringe steady, relative to the plunger, and/or move the barrel relative to the plunger.

Advantageously then, some embodiments disclosed herein increase the ease of performing aspiration and injection at a target site to ensure that the needle(s) is not within the blood vessel. Another advantage of some embodiments disclosed herein is the fact that aspiration and injection could be performed using a single hand. Using embodiments disclosed herein, a user's thumb can be used to engage the plunger head to move the plunger relative to the barrel. Yet another advantage of some embodiments disclosed herein is the ability to removably couple the flange extender with the barrel.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 7A is cross-section view of the flange extender of FIG. 6 along the line 7A-7A, according to some embodiments.

FIG. 7B is cross-section view of the flange extender of FIG. 6 along the line 7B-7B, according to some embodiments.

FIG. 8 is cross-section view of the flange extender of FIG. 6 along the line 8-8, according to some embodiments.

DETAILED DESCRIPTION

Figure 1:
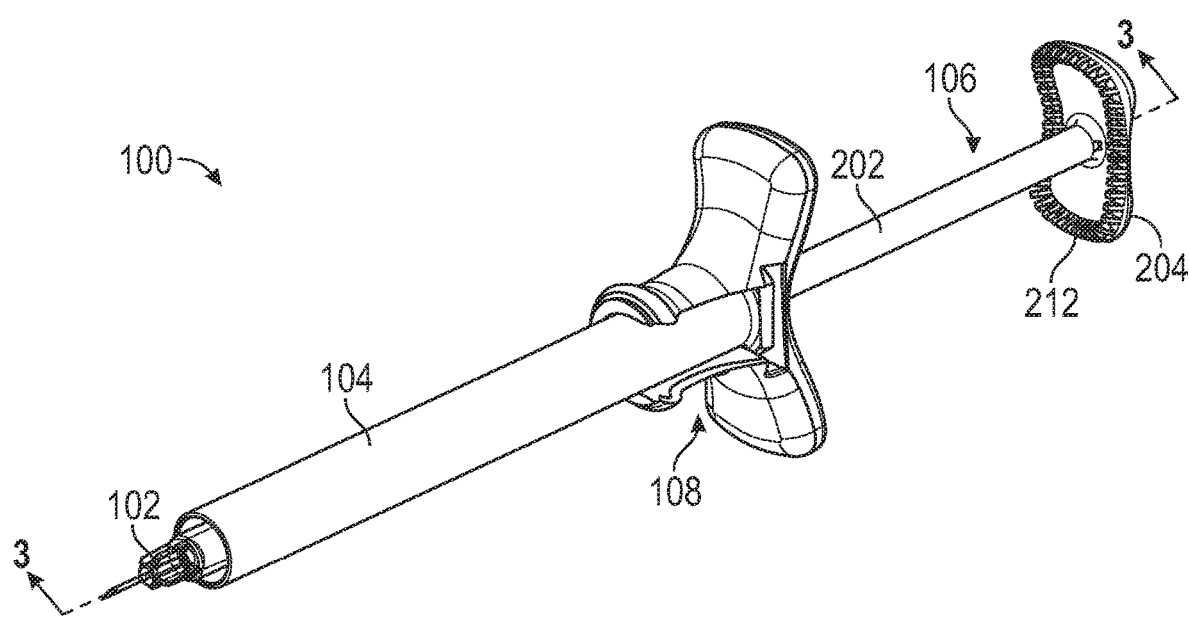
FIG. 1 is a front perspective view of an injection and aspiration device, according to some embodiments.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

The present disclosure addresses several operational challenges encountered with injection devices and related procedures. This disclosure provides numerous improvements that enable aspiration of a target site and ejection of a medicament from a syringe in an efficient, safe, and precise manner.

For example, in accordance with some embodiments, the present disclosure discloses a syringe that can be used to aspirate a target site to ensure a needle tip of the syringe is not located within a blood vessel, and to eject a medicament from the syringe using a single hand. In some embodiments of the device and related procedures disclosed herein can advantageously permit repositioning of a user's thumb between an aspiration position and an injection position.

In addition, some embodiments also provide for a modular flange extender system that can be implemented with existing syringe or syringe barrel products. The system can comprise a flange extender that has an engagement slot along a side thereof that provides access to a longitudinal bore of the flange extender. The barrel of the syringe can be inserted into the engagement slot to be removably engaged with the flange extender. In some embodiments, the flange extender can include an aperture or slot through which the plunger can be inserted or extend when the flange extender is coupled to the syringe barrel.

Further, some embodiments of the device and related procedures disclosed herein can advantageously provide an aspiration and injection device that can be used with existing medicament packaging techniques, such as standard sized syringes, e.g., 0.8 mL or 1 mL cyclic olefin copolymer (COC) syringe.

Although this disclosure describes the medicament as a gel, the medicament can be a substance configured to be ejected by a needle, including, liquids and gasses. In some implementations, the medicament is an injectable hyaluronic acid gel.

Figure 2:
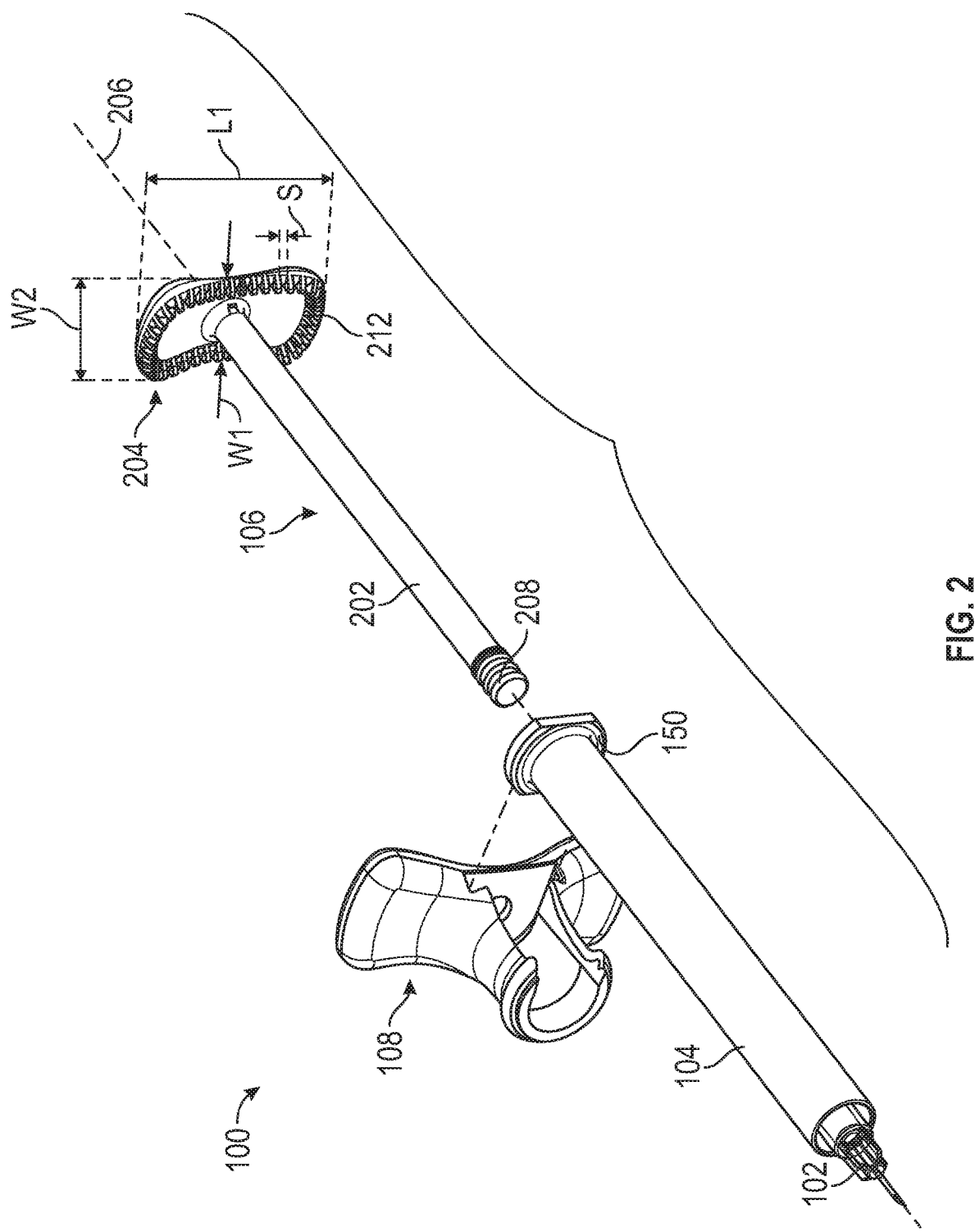
FIG. 2 is a partially exploded view of an injection and aspiration device, according to some embodiments.
Figure 3:
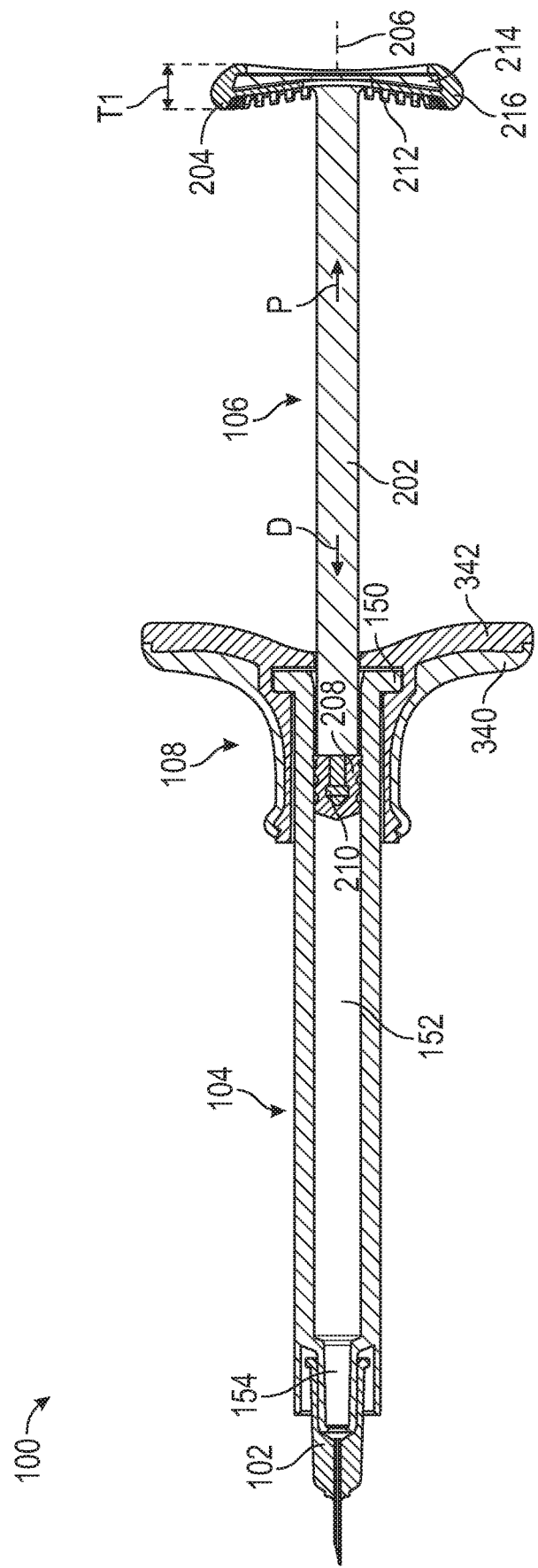
FIG. 3 is a side cross-section view of an injection and aspiration device of FIG. 1 along the line 3-3, according to some embodiments.

Referring to the figures, an aspiration and injection device 100 is illustrated in FIGS. 1-3. The device 100 can comprise a needle 102, a barrel 104, a plunger 106, and a flange extender 108.

The needle 102, the plunger 106, and the flange extender 108 can be coupled to the barrel 104. Any of the needle 102, the barrel 104, and/or plunger 106 can be a portion of an existing medicament packaging, such an existing syringe. The flange extender 108 can be a portion of the barrel 104, or a separate component assembled with to the barrel 104 and/or the plunger 106, as illustrated in FIG. 2.

The barrel 104 can have a proximal end portion, a distal end portion, and a flange 150. An inner surface of the barrel 104 can form an inner lumen 152 that extends from the proximal end portion toward the distal end portion of the barrel 104. The inner lumen 152 of the barrel can have a width or diameter that is approximately equal to or greater than a portion of the plunger 106 configured to be received therein. The diameter of the inner lumen 152 of the barrel can be at least about 3.5 mm and/or less than or equal to about 5.3 mm. Further, the diameter of the inner lumen 152 can also be between about 4 mm and about 5 mm, or between about 4.3 mm and about 4.7 mm. In some devices of the present disclosure, the diameter of the inner lumen 152 is about 4.6 mm.

The barrel 104 can have a passage 154 that extends from the inner lumen 152 to the distal end portion of the barrel 104 to permit a medicament to be ejected from the inner lumen 152. The needle 102 can be coupled to the distal portion of the barrel, and fluidly coupled to the passage 154. The needle 102 can be formed unitarily with the barrel 104 or coupled thereto. In some devices of the present disclosure, the needle 102 and barrel 104 include complementary luer fittings.

The flange 150 extends from a portion the barrel 104 and can be positioned at a proximal portion of the barrel 104. The flange 150 can be a portion of the barrel outer surface that extends radially away from the barrel 104. In some devices of the present disclosure, the flange 150 extends radially from a proximal-most end of the barrel 104, transverse to an axis through the longitudinal length of the barrel 104.

The barrel 104 can comprise an ejectable material therein. The ejectable material can be a medicament, for example, an ejectable gel such as a hyaluronic acid-based dermal filler. In some embodiments of the present disclosure, the barrel 104 is pre-filled with an ejectable material. The ejectable material is directed from the inner lumen 152, through the passage 154, by the plunger 106.

The plunger 106 can be moveably coupled with the barrel 104 to direct the ejectable material from the inner lumen 152, create a vacuum, and/or increase pressure within the inner lumen 152. The plunger 106 can comprise a plunger rod 202 and a plunger head 204. The plunger 106 can have a length between a proximal-facing surface of the plunger head to a distal end of the plunger rod. The length of the plunger 106 can be at least about 63.6 mm and/or less than or equal to about 95.4 mm. Further, the length of the plunger 106 can also be between about 71.5 mm and 87.4 mm, or between about 75.5 mm and about 83.4 mm. In some devices of the present disclosure, the length of the plunger 106 is about 79.5 mm.

In some implementations of the present disclosure, a plunger 106 having a length of about 76.52 mm can be used with a 0.8 mL COC syringe, and a plunger 106 having a length of about 81.92 mm can be used with a 1.0 mL COC syringe.

The plunger rod 202 can have a proximal end portion and a distal end portion. As shown in FIG. 2, the plunger 106 extends along a plunger axis 206 that extends between the proximal and distal end portions of the plunger 106.

An outer surface of the plunger rod 202 can have a cross-sectional dimension that is less than or equal to a cross-sectional dimension of the inner lumen 152 of the barrel to permit the plunger rod 202 to be moved along the plunger axis 206 within the inner lumen 152. In some devices of the present disclosure, the cross-sectional shape of the plunger rod 202 is approximately the same as a cross-sectional shape formed by the inner lumen of the barrel 104. A cross-sectional shape of the plunger rod 202 and/or the inner lumen of the barrel 104 can include any regular or irregular shape. In some implementations, the cross-sectional shape of the plunger rod 202 and/or the inner lumen of the barrel 104 can be any of a square, rectangle, triangle, and circle.

In some embodiments, the cross-sectional shape of the plunger rod 202 is a circle having a cross-sectional diameter. The cross-sectional diameter of the plunger rod 202 can be at least about 3.5 mm and/or less than or equal to about 5.5 mm. Further, the cross-sectional diameter of the plunger rod 202 can also be between about 4.0 mm and about 5.1 mm, between about 4.2 mm and about 4.8 mm, or between about 4.4 mm and about 4.6 mm.

In some implementations of the present disclosure, a plunger rod 202 having a cross-sectional diameter of about 4.6 mm can be used with a 0.8 mL COC syringe. A plunger rod 202 having a cross-sectional diameter of about 5.0 mm or about 6.5 mm can be used with a 1.0 mL COC syringe, and a plunger rod 202 having a cross-sectional diameter of about 8.75 mm can be used with a 2.25 mL COC syringe.

In some embodiments, the plunger rod 202 tapers from the proximal end portion toward the distal end portion. For example, the cross-sectional diameter of the plunger rod 202 at the proximal end portion can be at least about 3.7 mm and/or less than or equal to about 9.75 mm. Further, the cross-sectional diameter of the plunger rod 202 at the distal end portion can also be between about 3.5 mm and about 5.3 mm, between about 4 mm and about 5 mm, or between about 4.3 mm and about 4.7 mm. In some embodiments, a plunger rod 202 having a cross-sectional diameter that tapers from about 4.38 mm at the proximal end portion to about 4.04 mm at the distal end portion can be used with a 0.8 mL COC syringe. A plunger rod 202 having a cross-sectional diameter that tapers from about 4.6 mm at the proximal end portion to about 4.4 mm at the distal end portion can be used with a 1.0 mL COC syringe.

In some embodiments, a portion of the plunger rod 202 can taper from the proximal end portion toward the distal end portion. The plunger rod 202 can taper at angle of at least about 0.1 degrees and/or less than or equal to about 0.3 degrees. Further, the plunger rod 202 can also taper between about 0.15 degrees and about 0.18 degrees, or between about 0.16 degrees and about 0.17 degrees. In some devices of the present disclosure, the plunger rod 202 tapers at an angle of about 0.165 degrees. In some implementations of the present disclosure, a plunger rod 202 having a cross-sectional diameter that tapers at angle of 0.26 degrees can be used with a 0.8 mL COC syringe.

The length of the plunger rod 202 can be at least about 53.8 mm and/or less than or equal to about 88.8 mm. Further, the length of the plunger rod 202 can also be between about 66.6 mm and about 81.4 mm, between about 70.3 mm and about 77.7 mm, or between about 73.0 mm and about 75.0 mm. In some devices of the present disclosure, the length of the plunger rod 202 is about 74.0 mm.

In some implementations of the present disclosure, a plunger rod 202 having length of 68.2 mm can be used with a 0.8 mL COC syringe, and a plunger rod 202 having length of 72.8 mm can be used with a 1.0 mL COC syringe.

A distal portion of the plunger rod 202 can include a distal shaft 210. The distal shaft 210 can have a groove extends around a circumference of the distal shaft 210 to permit a portion of a plunger piston to be attached thereto. A portion of the outer surface of the distal shaft 210, along the groove, can taper to away from the plunger rod 202. The distal shaft 210 can have a length of at least about 4.2 mm and/or less than or equal to about 6.4 mm. Further, the length of the distal shaft 210 can also be between about 4.8 mm and about 5.8 mm, between about 5.0 mm and about 5.6 mm, or between about 5.2 mm and about 5.4 mm. In some embodiments, the distal shaft 210 length is about 5.3 mm.

In some devices of the present disclosure, the distal end portion of the plunger rod 202 includes a piston 208 to engage against the inner surface of the barrel 104. The piston 208 can be coupled to the plunger rod 202 or formed unitarily with the plunger rod 202. In some embodiments, the piston 208 can be coupled to the distal shaft 210 of the plunger 106. An outer surface of the piston 208 engages against an inner surface of the barrel 104 along the inner lumen 152 to form a sealing interface. The sealing interface between the piston 208 and the inner surface of the barrel 104 permits the creation of pressure and/or vacuum within the inner lumen 152 when the plunger 106 is moved relative to the barrel 104. In some implementations, when the plunger rod 202 is moved into the inner lumen 152, the piston 208 engages against and directs an ejectable material out of the barrel 104.

The proximal end portion of the plunger 106 includes the plunger head 204, which can be grasped by a user of the device 100 to move the plunger 106 relative to the barrel 104. The plunger head 204 can be coupled to the proximal end portion of the plunger rod 202 or formed unitarily with the plunger rod 202. The plunger head 204 can permit movement of the plunger 106 around the plunger axis 206, in a distal direction (arrow D), and a proximal direction (arrow P).

The plunger head 204 extends radially from the plunger rod 202. In some embodiments, the plunger head 202 extends transverse to the plunger axis 206. The plunger head 204 can include planar surfaces having a cross-sectional profile transverse to the plunger axis 206. The profile of the plunger head 204 can include a rectangle, a square, a circle, or any other shape or combination thereof. In some devices of the present disclosure, a profile of the plunger head 204 includes a sphere, a hyperbolic paraboloid (e.g., saddle) shape, and/or an arch. Portions of the arch can extend toward the distal end portion of the plunger rod 202.

In some devices of the present disclosure, the plunger head 204 comprises a generally rectangular cross-sectional profile having a length L1 and a width. The length L1 of the generally rectangular plunger head 204 can be at least about 21.3 mm and/or less than or equal to about 32.0 mm. Further, the length L1 can also be between about 23.9 mm and about 29.3 mm, between about 25.3 mm and about 27.9 mm, or between about 25.9 mm and about 27.3 mm. In some embodiments, the plunger head length L1 is about 27.16 mm.

The width of the generally rectangular plunger head 204 can be at least about 10.4 mm and/or less than or equal to about 19.0 mm. Further, the width can also be between about 11.7 mm and about 16.1 mm, between about 12.4 mm and about 15.3 mm, or between about 12.7 mm and about 15.0 mm. In some embodiments, the plunger head width is 14.0 mm.

In some devices, the width of the generally rectangular plunger head 204 tapers away from the plunger axis 206, from a first width W1 to a second width W2. The first width W1 of the plunger head 204 can be at least about 10.4 mm and/or less than or equal to about 15.7 mm. Further, the first width W1 can also be between about 11.7 mm and about 14.4 mm, between about 12.4 mm and about 13.7 mm, or between about 12.7 mm and about 13.4 mm. In some embodiments, the plunger head first width W1 is about 13.26 mm.

The second width W2 of the plunger head 204 can be at least about 11.7 mm and/or less than or equal to about 19.0 mm. Further, the first width W1 can also be between about 13.1 mm and about 16.1 mm, between about 13.9 mm and about 15.3 mm, or between about 14.2 mm and about 15.0 mm. In some embodiments, the plunger head second width W2 is about 14.6 mm. In some embodiments, the width of the generally rectangular plunger head 204 varies along the length L1, between a first width W1 to a second width W2.

The plunger head 204 can have a distal-facing surface, which faces toward the distal end portion of the plunger 106, and a proximal-facing surface, which is opposite the distal-facing surface.

The proximal-facing surface of the plunger head 204 can have a concave surface configured to be engaged by a thumb or other portion of a user's hand to move the plunger 106 relative to the plunger axis 206. In some examples, the proximal-facing surface of the plunger head 204 is engaged by a digital pulp or thumb pad of a user to move the plunger 104 distally into the inner lumen 152 of the barrel.

The distal-facing surface of the plunger head 204 can be engaged by a fingertip or nail of a user to move or withdraw the plunger 106 proximally from the inner lumen 152 of the barrel. At least a portion of the distal-facing surface can have a concave surface to provide a contoured surface for engagement by a user to move the plunger 104 proximally for withdrawal of the plunger 106 from the inner lumen 152 of the barrel.

The plunger head 204 can include a surface structure that is engaged by a portion of a fingertip and/or fingernail of a user to move the plunger 104 proximally for withdrawal of the plunger 106 from the inner lumen 152 of the barrel. The surface structure assists a user to engage or grasp the plunger head 204 with a fingertip, enabling the user to more easily move the plunger 106 in the proximal direction for performing the aspiration step.

The surface structure can include a plurality of engagement structures 212 that extend away from the plunger head 204. The plurality of engagement structures 212 can be positioned on the distal-facing surface of the plunger head 204. The plurality of engagement structures 212 extend toward the distal end portion of the plunger rod 202. In some devices and methods of the present disclosure, the plurality of engagement structures 212 are positioned along a perimeter of the plunger head 204, such that the engagement structures 212 extend radially outward from the plunger axis 206 and toward the distal end portion of the plunger rod 202.

The plurality of engagement structures 212 can include any of ridges, protrusions, dimples, grooves, recesses, and combinations thereof. In some examples, the surface structure is a continuous ridge or groove on the plunger head 204. The plurality of engagement structures 212 can define a distal plane, wherein a portion of the distal plane is concave.

A portion of the plunger head 204, radially inward of the surface structure, can form a distal-facing recess. The recess is offset from the distal plane formed by the plurality of engagement structures 212.

Referring to FIG. 2, the plurality of engagement structures 212 can include ridges that extend radially relative to the plunger axis. The ridges are positioned in a radiating orientation to form a distally projecting ring, which circumscribes the plunger rod 202. The plurality of engagement structures 212 or ridges can be spaced apart by a distance S to permit a fingernail or fingertip to be at least partially positioned between adjoining engagement structures of the plurality of engagement structures 212. Adjoining engagement structures of the plurality of engagement structures 212 can be spaced apart by a distance S of at least about 0.5 mm and/or less than or equal to about 2.0 mm.

The plunger head 204 can have a thickness T1 that extends between the distal and proximal-facing surfaces. The thickness T1 of the plunger head 204 can be at least about 3.9 mm and/or less than or equal to about 5.8 mm. Further, the thickness T1 can also be between about 4.4 mm and about 5.4 mm, between about 4.6 mm and about 5.1 mm, or between about 4.7 mm and about 5.0 mm. In some embodiments, the plunger head thickness T1 is about 4.9 mm.

In some embodiments, the thickness of the plunger head 204 tapers away from the plunger axis 206, from a minimum thickness to a maximum thickness. The plunger head 204 can taper from a minimum thickness of at least about 3.9 mm to a maximum thickness of less than or equal to about 5.0 mm. Further, the thickness can taper between about 4.4 mm and about 5.4 mm, between about 4.6 mm and about 5.1 mm, or between about 4.7 mm and about 5.0 mm. In some embodiments, the plunger head 204 taper s to a maximum thickness of about 4.9 mm.

To move the plunger 106 in the proximal direction, relative to the barrel 104, a fingernail or fingertip can be engaged between adjoining engagement structures, and a proximal force in a wide range of angles applied to the plunger head 204. The plurality of engagement structures 212 can also be engaged by a user to move the plunger 106 in the distal direction, relative to the barrel 104.

The plunger 106 can be formed or assembled from two or more materials. In some embodiments, the plunger 106 includes a first material 214 and a second material 216, where the second material is more flexible relative to the first material. The second material 216 can comprise a soft polymer or resilient material that provides enhanced friction when engaged by a user, relative to the first material 214.

The first material 214 can define a first portion of the plunger 106 that includes the plunger rod 202 and a portion of the plunger head, and the second material 216 can define a second portion of the plunger 106. The second portion of the plunger can comprise the plurality of engagement structures 212, such that the plurality of engagement structures 212 are formed by the second material 216. The second material 216 can also extend along any of the proximal-facing surface and perimeter of the plunger head 204. In some devices of the present disclosure, the second material 216 extends from a perimeter of the proximal-facing surface to the distal-facing surface of the plunger head 204. In some devices, the entire plunger head 204 can be formed by the second material 216.

The first material 214 can comprise a rigid polymer that resists flexing during use or operation of the device. For example, the plunger rod 202 may comprise a moldable polymer and may include a glass-filled polymer or other similar material that will increase rigidity of the plunger rod 202 to thereby reduce flexing. The rigidity of the plunger rod 202 or other portions of the plunger 106 permit precise user control during movement of the plunger 106 relative to the barrel 104.

The second portion of the plunger can be formed over or around the first portion using an overmolding process. In some devices of the present disclosure, the first and second portions are assembled together using any of a fastener, bonding material, and/or weld.

FIG. 3 illustrates the plunger 106 coupled with the barrel 104. The plunger 106 can be coupled with the barrel 104 by inserting the distal end portion of the plunger rod 202 into the inner lumen 152 of the barrel. With the distal end portion of the plunger rod 202 within the inner lumen 152 of the barrel, the proximal end portion of the plunger rod 202, including the plunger head 204, extends from the barrel 104. A sealing interface is created between the outer surface of the plunger rod 202 and the inner surface of the barrel 104. In some embodiments, the piston 208 sealingly engages against the inner surface of the barrel 104.

When the plunger 106 is coupled with the barrel 104, the distal end portion of the plunger 106 can be linearly moved along the inner lumen of the barrel 104, between the proximal and distal end portions of the barrel 104. The plunger 106 can also be rotatably moved on the plunger axis 206 to prevent a line of sight by the user from being obstructed by the plunger head 204.

Figure 4:
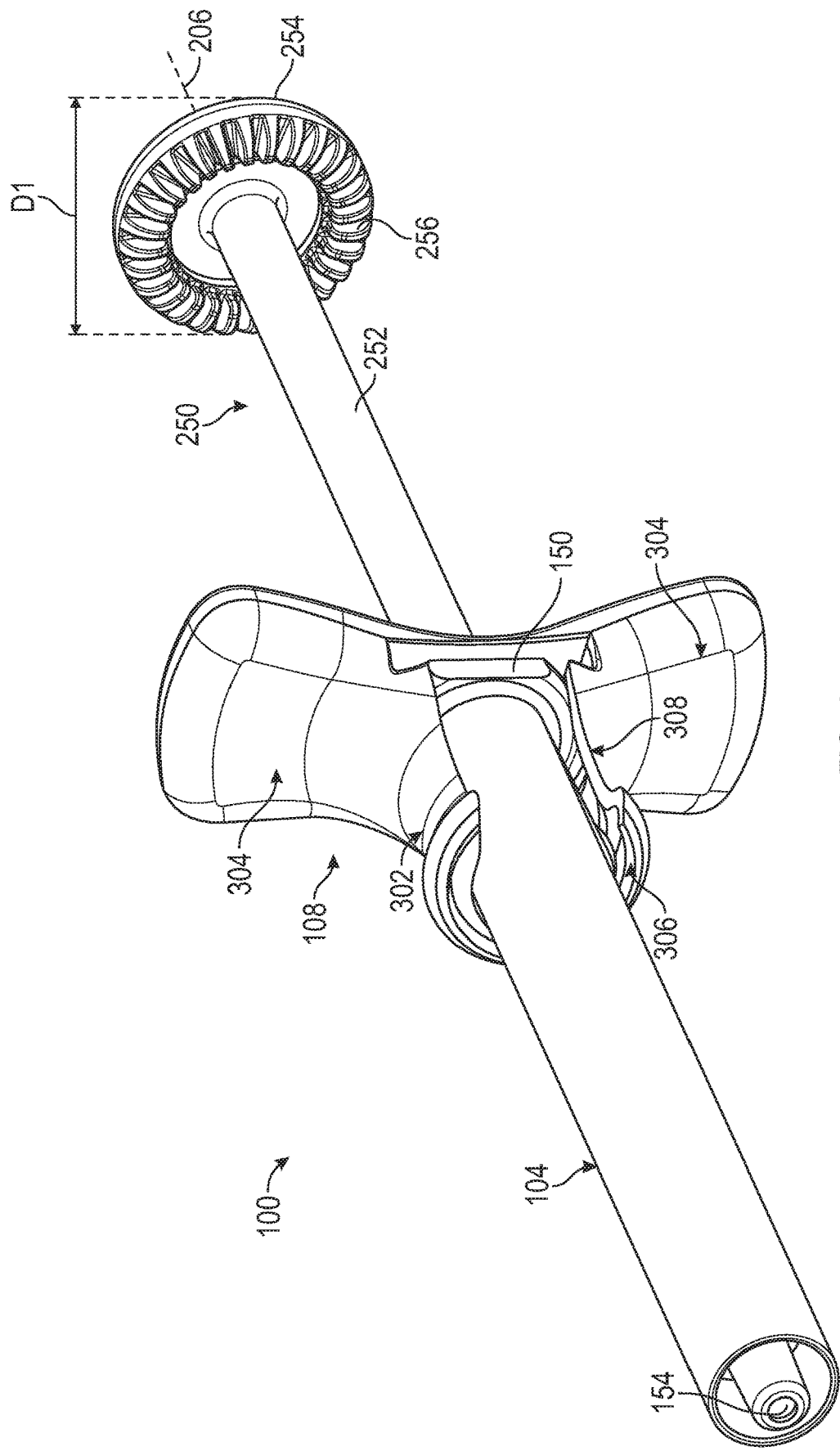
FIG. 4 is a front perspective view of an injection and aspiration device, according to some embodiments.

Referring to FIG. 4, an aspiration and injection device 100 is illustrated with a circular plunger head, and having features like those described with regard to FIGS. 1-3. For clarity and brevity, the general features in common with the aspiration and injection device 100 of FIGS. 1-3 are not repeated here.

The aspiration and injection device 100 can comprise a barrel 104, a flange extender 108, and a plunger 250. The plunger 250 can have a proximal end portion and a distal end portion, and a plunger axis 206 that extends between the proximal and distal end portions of the plunger 250. The plunger distal end portion includes a plunger rod 252 and the proximal end portion includes a plunger head 254.

The plunger head 254 comprises a generally circular profile having a diameter. The diameter D1 of the circular plunger head 254 can be at least about 14.2 mm and/or less than or equal to about 21.2 mm. Further, the diameter D1 can also be between about 15.9 mm and about 19.5 mm, between about 16.8 mm and about 18.6 mm, or between about 17.3 mm and about 18.1 mm. In some embodiments, the plunger head width is about 17.7 mm.

The plunger head 254 can have a thickness that extends between a distal-facing surface and a proximal-facing surface. The thickness of the plunger head 254 can be at least about 4.4 mm and/or less than or equal to about 6.6 mm. Further, the thickness can also be between about 4.9 mm and about 6.0 mm, between about 5.2 mm and about 5.7 mm, or between about 5.3 mm and about 5.6 mm. In some embodiments, the plunger head thickness is about 5.5 mm.

The plunger head 254 includes a plurality of engagement structures 256 that extend away from the plunger head 254. The plurality of engagement structures 256 are be positioned on a distal-facing surface of the plunger head 254, and extend toward the distal end portion of the plunger rod 252. The plurality of engagement structures 256 are aligned along a perimeter of the plunger head 254 to form a ring. The plurality of engagement structures 256 can include ridges that extend radially relative to the plunger rod 252. The ridges are positioned in a radiating orientation to form a distally projecting ring, which circumscribes the plunger rod 252.

Referring to FIGS. 4-7B, the aspiration and injection device 100 can include a flange extender 108 that can be coupled to the barrel 104 to increase the surface area of the barrel flange 150 and permit the user to achieve a steady grip on the aspiration and injection device 100.

The flange extender 108 can include a central body 302 having a proximal end and a distal end, and grip members 304 that extend from the central body 302. A longitudinal bore 306 extends between the proximal and distal ends of the central body 302, and is configured to receive a portion of the barrel 104 therein. An engagement slot 308 extends from a side surface of the central body 302 into the longitudinal bore 306 to permit insertion thereinto of a portion of the barrel 104.

The central body 302 can have a proximal end and a distal end, and a longitudinal length between the proximal and distal ends. A cross-sectional dimension of the central body 302 can vary between the proximal and distal ends. In some implementations of the present disclosure, the cross-sectional dimension tapers toward the proximal and distal ends. Along a distal end portion of the central body 302, the cross-sectional dimension can taper to a length L2. The length L2 can be at least about 13.8 mm and/or less than or equal to about 20.8 mm. Further, the length L2 can also be between about 15.6 mm and about 19.0 mm, between about 16.4 mm and about 18.2 mm, or between about 16.9 mm and about 17.7 mm. In some embodiments, the length L2 is about 17.3 mm.

The grip members 304 extend from the central body 302 to provide a surface for a user to grasp the aspiration and injection device 100. For example, a user can grasp the grip members 304 using one or more finger, such as an index and middle finger, or using opposing a thumb and one or more opposing finger.

To provide a surface for a user to grasp the device, the grip members 304 extend transverse to a longitudinal length between the proximal and distal ends of the central body 302. The grip members 304 can extend in any direction, including radially opposing directions to form a T-shape with the central body 302.

Along a proximal end portion of the central body 302, a cross-sectional dimension of the central body 302 can have a length L3 extending between radially opposing ends of the grip members 304. The length L3 can be at least about 33.8 mm and/or less than or equal to about 50.6 mm. Further, the length L3 can also be between about 38.0 mm and about 46.4 mm, between about 40.1 mm and about 44.3 mm, or between about 41.1 mm and about 43.3 mm. In some embodiments, the length L3 is about 42.11 mm.

Figure 5:
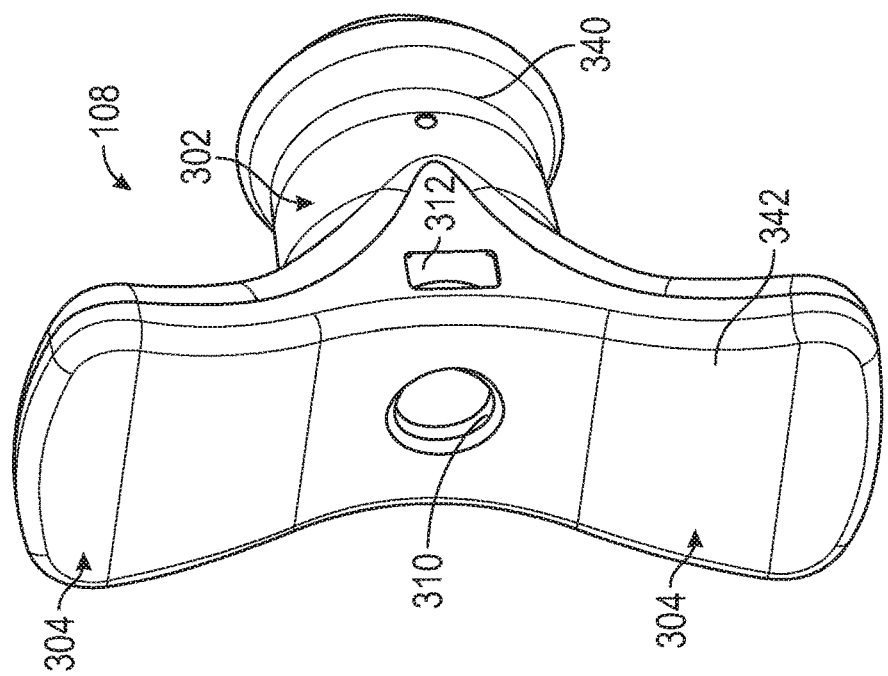
FIG. 5 is a rear perspective view of a flange extender, according to some embodiments.

The grip members can include a distal-facing surfaces (FIG. 4) and proximal-facing surfaces (FIG. 5). The distal and proximal-facing surfaces can have portions forming concave and/or convex surfaces to provide ergonomic engagement of a user's hand or fingers against the grip members 304.

To provide the ergonomic features, a first portion of the proximal-facing surface can have a concave surface, and a second portion of the proximal-facing surface can have a convex surface. The concave surface of the proximal-facing surface can be positioned along an inner portion of the grip members 304 proximal to the central body 302, and outer portions of the proximal-facing surface, distal to the central body 302, can have convex surfaces. At least a portion of the distal-facing surface of the flange extender 108 can comprise a concave surface. Where the flange extender 108 comprises radially extending grip members 304, each of the radially extending grip members 304 can have a concave distal-facing surface.

In some devices and methods, the flange extender 108 comprises a single grip member or a plurality of grip members. The grip member can be any of a circular radially extending flange, a ring that circumscribes and is spaced apart from the central body 302, one or more outwardly extending handle, and any combination or similar structure that permits a user to grasp the flange extender 108.

A plunger bore 310 can extend through the proximal end of the central body 302 to the longitudinal bore 306 to permit insertion therethrough of a portion of the plunger 106. A diameter of the plunger bore 310 can be at least about 3.8 mm and/or less than or equal to about 5.8 mm. Further, the diameter can also be between about 4.3 mm and about 5.3 mm, between about 4.6 mm and about 5.0 mm, or between about 4.7 mm and about 4.9 mm. In some embodiments, the diameter of the plunger bore 310 is about 4.8 mm.

A side aperture 312 can extend from the side surface of the central body 302, opposite the engagement slot 308, into the longitudinal bore 306. The side aperture 312 can be used to separate a flange extender 108 from a barrel 104 positioned within the longitudinal bore 306. To separate a flange extender 108 from a barrel 104, the flange 150 can be engaged through the side aperture 312, and directed toward the engagement slot 308, opposite the side aperture 312. The side aperture 312 can have a height extending between the proximal and distal ends of the central body 302. The height of the side aperture 312 can be at least about 2.0 mm and/or less than or equal to about 3.0 mm. Further, the height can also be between about 2.3 mm and about 2.8 mm, between about 2.4 mm and about 2.6 mm, or between about 2.4 mm and about 2.6 mm. In some embodiments, the height of the side aperture 312 is about 2.5 mm.

Figure 6:
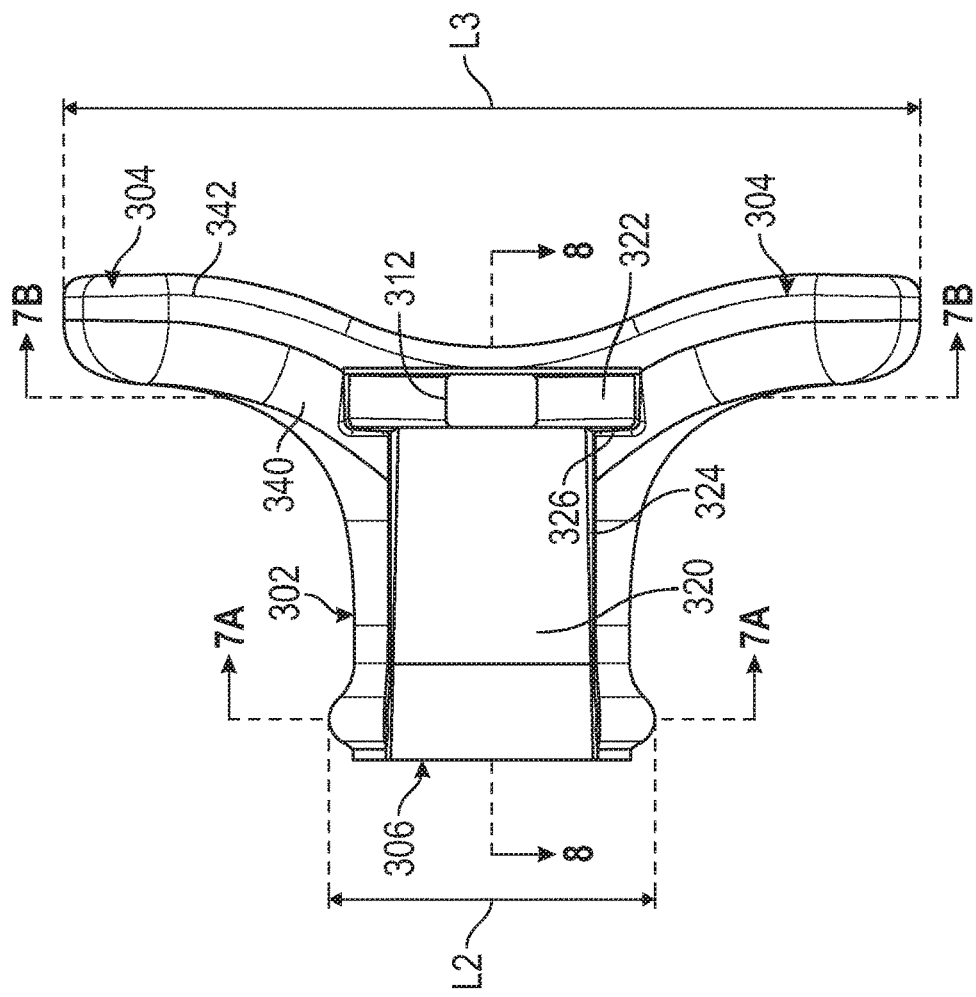
FIG. 6 is a side view of a flange extender, according to some embodiments.

Referring to FIGS. 6-7B, the longitudinal bore 306 can include one or more portions, including a barrel bore 320 and a flange bore 322. The barrel bore 320 and a flange bore 322 can have a different size and/or shape adapted to receive a portion of the barrel 104 and the flange 150, respectively.

The barrel bore 320 can be positioned along a distal portion of the longitudinal bore 306 to receive a portion of the barrel 104 adjacent to the flange 150 when the flange extender 108 is coupled to the barrel 104. The barrel bore 320 can extend from the distal end toward the proximal end of the flange extender 108.

Referring to FIG. 7A, the barrel bore 320 comprises a cross-sectional length or barrel bore diameter D2. The barrel bore diameter D2 is approximately equal to or larger than a cross-sectional length or diameter of the barrel 104. The barrel bore diameter D2 can be at least about 7.7 mm and/or less than or equal to about 11.5 mm. Further, the diameter D2 can also be between about 8.6 mm and about 10.6 mm, between about 9.1 mm and about 10.1 mm, or between about 9.4 mm and about 9.8 mm. In some embodiments, the barrel bore diameter D2 is about 9.3 mm.

To insert the portion of the barrel 104 and the flange 150 into the longitudinal bore 306, the barrel 104 and the flange 150 are moved through the engagement slot 308. The engagement slot 308 can include one or more portions, including a barrel slot 324 and a flange slot 326.

The barrel slot 324 extends, along its length, from a side surface of the central body 302 into the longitudinal bore 306 to permit insertion thereinto of a portion of the barrel 104. The barrel slot 324 can have a width W3 at the intersection of the barrel slot 324 with the barrel bore 320.

The width W3 can be less than the barrel bore diameter D2 to restrict movement of a barrel 104, positioned within the longitudinal bore 306, toward the side surface of the central body 302. The width W3 can be at least about 7.3 mm and/or less than or equal to about 10.9 mm. Further, the width W3 can also be between about 8.2 mm and about 10.0 mm, between about 8.6 mm and about 9.6 mm, or between about 8.9 mm and about 9.3 mm. In some embodiments, the width W3 is about 9.1 mm.

The width W3 of the barrel slot 324 at the intersection of the barrel slot 324 with the barrel bore 320 can be a factor of the barrel bore diameter D2. For example, the width W3 can be 80-90% of the maximum barrel bore diameter D2.

The width of the barrel slot 324 can taper away from the barrel bore 306 toward the side surface of the central body 302. The barrel slot 324 can taper away from the intersection of the barrel slot 324 with the barrel 324 at an angle A1 of about 10 degrees.

In some devices of the present disclosure, the engagement slot 308 comprises clip-on structures to permit a portion of the barrel 104 to be inserted through the engagement slot 308, yet restrict movement of a barrel 104 from the longitudinal bore 306 toward the side surface of the central body 302. The clip-on structures can comprise any structure that can be urged to permit intentional movement of a barrel 104 through the engagement slot 308, yet prevents movement of the barrel 104 from the engagement slot 308 under normal use. The clip-on structures can extend from opposing sections of the engagement slot 308 to define a width that is less than a maximum diameter of the longitudinal bore 306.

The clip-on structures can comprise a reduced width portion of the engagement slot 308. The reduced width portion can be formed by opposing inner surfaces of the engagement slot 308 that converge from a maximum width proximal to the side surface of the central body 302 to a reduced width and then diverge to the maximum width proximal to the longitudinal bore 306.

Referring to FIG. 7B, a proximal portion of the longitudinal bore 306 can include the flange bore 322 to receive the flange 150 of the barrel 104 when the flange extender 108 is coupled to the barrel 104. The flange bore 322 comprises a cross-sectional length or flange bore diameter D3. The flange bore diameter D3 is approximately equal to or greater than a cross-sectional length of the flange 150. The flange bore diameter D3 can be at least about 11.2 mm and/or less than or equal to about 16.8 mm. Further, the flange bore diameter D3 can also be between about 12.6 mm and about 15.4 mm, between about 13.3 mm and about 14.7 mm, or between about 13.7 mm and about 14.4 mm. In some embodiments, the flange bore diameter D3 is about 14.0 mm. Generally, the flange bore diameter D3 is larger than the barrel bore diameter D2.

The flange slot 326 is adjacent to and contiguous with the barrel slot 324, between the proximal and distal ends of the central body 302. The flange slot 326 extends, along its length, from a side surface of the central body 302 into the longitudinal bore 306 to permit insertion thereinto of the flange 150. The flange slot 326 can have a width W4 at the intersection of the flange slot 326 with the flange bore 322. The width W4 can be approximately equal to or greater than the flange bore diameter D3 to permit unrestricted movement of the flange 150 between the flange bore 322 and the side surface of the central body 302. In some embodiments, the width W4 can be less than the flange bore diameter D3 so restrict movement of a flange 150, positioned within the longitudinal bore 306, toward the side surface of the central body 302.

Referring to FIG. 8, the flange slot 326 can have a height that extends between the proximal and distal ends of the central body 302. In some devices of the present disclosure, the height of the flange slot 326 can taper from the side surface of the central body toward the longitudinal bore 306. The height of the flange slot 326 can taper from a first height H1, proximal to a side surface of the central body 302 comprising the engagement slot 308, to a second height H2, proximal to a side surface of the central body 302 opposite the engagement slot 308. In some implementations, the flange slot 326 intersects the side aperture 312 so that the second height H2 can be about the same height as the side aperture 312. A portion of the flange slot 326 can extend from the side surface of the central body through the side aperture 312. When a barrel 104 is positioned within the longitudinal bore 306, the tapered flange slot 326 can engage against and restrict movement of the flange 150 toward the side surface of the central body 302.

The first height H1 can be at least about 1.8 mm and/or less than or equal to about 3.4 mm. Further, the first height H1 can also be between about 2.6 mm and about 3.1 mm, between about 2.7 mm and about 3.0 mm, or between about 2.8 mm and about 2.9 mm. In some embodiments, the first height H1 is about 2.8 mm The second height H2 can be at least about 1.7 mm and/or less than or equal to about 3.0 mm. Further, the second height H2 can also be between about 2.3 mm and about 2.8 mm, or between about 2.4 mm and about 2.6 mm. In some embodiments, the second height H2 is about 2.5 mm.

The flange extender 108 can be formed or assembled from two or more materials. In some devices and methods, the flange extender 108 includes a first material 340 and a second material 342, where the second material 342 is more flexible relative to the first material 340. The second material 342 can comprise a soft polymer or resilient material that provides enhanced friction when engaged by a user, relative to the first material 340.

The first material 340 can define a first portion of the flange extender 108 that includes the central body 302 and the grip members 30, and a second portion of the plunger can define a second portion of the flange extender 108. The second portion of the flange extender 108 can comprise a proximal-facing surfaces of the grip members 304 to provide a resilient surface to be engagement by a user's hand or fingers when the plunger 106 and barrel 104 are moved away from each other. In some embodiments, the entire flange extender 108 can be formed of the second material 342. The second portion of the flange extender 108 can be formed over or around the first portion using an overmolding process. In some embodiments, the first and second portions are assembled together using any of a fastener, bonding material, and/or weld.

The second material 342 can also extend along any of an outer and inner surface of the flange extender 108. The second material 342 extends along the proximal-facing surfaces of the grip members 304 and an inner surface of the longitudinal bore 306 and/or the engagement slot 308.

Referring to Referring to FIG. 8, the second material 342 extends along an inner surface of the longitudinal bore 306 and the engagement slot 308.

The second material 342 extends along at least a portion of the engagement slot 308 to restrict movement of a barrel 104 through the engagement slot 308. In particular, the second material 342 extends along the barrel slot 324 to be resiliently urged when a barrel 104 is moved through the barrel slot 324 into the longitudinal bore 306. The larger friction coefficient and resiliency of the second material 342, relative to the first material 340, can prevent movement of the barrel 104 from the longitudinal bore 306 toward the side surface of the central body 302.

The second material 342 also extends along at least a portion of an inner surface of the longitudinal bore 306 to restrict movement of a barrel 104 relative to the longitudinal bore. In particular, the second material 342 extends along the flange slot 326 and the flange bore 322 to be resiliently urged when a flange is inserted therein. The tendency of the second material 342 to return to a neutral or orientation causes the flange 150 of the barrel 104 to be retained within the flange slot 326 and the flange bore 322.

The first material 340 can comprise a similar and/or same material as the first material 214 of the plunger 106, such as a rigid polymer that resists flexing during use or operation of the device. For example, the flange extender 108 may comprise a moldable polymer and may include a glass-filled polymer or other similar material that will increase rigidity of the flange extender 108 to thereby reduce flexing. The rigidity of the central body 302 and/or grip members 304 permit precise user control during movement of the plunger 106.

A flange extender 108 can be assembled with a barrel 104 and plunger 106, as illustrated in FIGS. 1-3.

To assemble a flange extender 108, a portion of the barrel 104 is inserted through the engagement slot 308, such that the portion of the barrel 104 is positioned within the longitudinal bore 306. The barrel 104 can be positioned within the longitudinal bore 306 so that the barrel is received within the barrel bore 320 and the flange 150 is received within the flange bore 322.

To position the barrel 104 within the longitudinal bore 306, the barrel 104 is inserted through the engagement slot 308. In particular, a portion of the barrel 104 is moved through the barrel slot 326. When the barrel 104 is moved through the barrel slot 326, a portion of the central body 302, which can include the second material 342 and/or clip-on structures, is urged by to the barrel 104 to permit movement of the barrel 104 therethrough.

As the barrel 104 is moved through the barrel slot 326, the flange 150 is moved through the flange slot 326, which can include the second material 342. Because the height of the flange slot 326 tapers toward the longitudinal bore 306, a portion of the central body 302, which can include the second material 342, is urged by the flange 150 to permit movement of the flange 150 into the flange bore 322.

A plunger 106 can be assembled with the flange extender 108 and the barrel 104 by coupling a portion of the plunger 106 with the barrel 104. The plunger 106 is coupled with the barrel by inserting a portion of the plunger through the proximal end of the central body 302, such that the portion of the plunger is positioned within the inner lumen 152 of the barrel. The plunger 106 can be inserted through the proximal end of the central body 302 by moving the distal end portion of the plunger rod 252 through the plunger bore 310, which is aligned with the inner lumen 152 when the barrel 104 is positioned within the longitudinal bore 306.

In some devices of the present disclosure, the flange extender can be coupled to a preassembled syringe in which the plunger is already coupled to the barrel. For example, the flange extender 108 can include a plunger slot through which the plunger rod can to pass to permit assembly of the flange extender 108 with the pre-assembled syringe. To permit assembly with the pre-assembled syringe, the plunger slot can extend from a side surface of the central body 302 to the plunger bore 310. The plunger slot can be adjacent to and contiguous with the engagement slot 308 so that these slots collectively form a continuous slot that extends between the proximal and distal ends of the central body 302. During assembly of a flange extender 108 with a pre-assembled syringe, the barrel and plunger can be inserted through the continuous slot, such that a portion of the barrel 104 is positioned within the longitudinal bore 306, and a portion of the plunger 106 is positioned within the plunger bore 310.

The aspiration and injection device 100 can be used to perform aspiration of a target site and/or eject a medicament using a variety of hand grip positions. Aspiration and ejection can be performed using one or more hand, one or more finger, and any combination of hands and/or fingers. To illustrate some of the variety of hand grip positions, several non-limiting examples are included here.

To perform an aspiration, the plunger 106 and barrel 104 are moved away from each other. To move the plunger 106 and barrel 104 away from each other, a user can place a one or more finger on the barrel 104 and/or the flange extender 108, and one or more finger, such as a thumb, on the distal-facing surface of the plunger head 204. The barrel 104 and/or the flange extender 108 can be grasped by placing a one or more finger, such as an index and middle finger, on the distal-facing surface of the flange extender 108. By grasping the barrel 104 and/or flange extender 108 between the user's fingers, the device can be steadily retained while the user's thumb is retracted to proximally withdraw the plunger 106, thereby creating a vacuum within the inner lumen 152.

In another example, the barrel 104 and/or flange extender 108 are grasped between the user's thumb and one or more finger, while the plunger head 204 is retained by the closed palm and/or thumb pad of the user. By extending the user's thumb and one or more finger, the plunger 106 and barrel 104 are moved away from each other.

To eject a medicament, the plunger 106 and barrel 104 are moved toward each other. To move the plunger 106 and barrel 104 toward each other, a user can place a one or more finger on the barrel 104 and/or the flange extender 108, and one or more finger, such as a thumb, on the proximal-facing surface of the plunger head 204. The barrel 104 and/or the flange extender 108 can be grasped by placing a one or more finger, such as an index and middle finger, on the distal-facing surface of the flange extender 108. By grasping the barrel 104 and/or flange extender 108 between the user's fingers, the device can be steadily retained while the user's thumb is advanced to move the plunger 106 into the barrel 104.

In another example, the barrel 104 and/or flange extender 108 is grasped between one or more finger, while the plunger head 204 is engaged against the palm and/or thumb pad of the user. The barrel 104 and/or the flange extender 108 can be grasped by placing a one or more finger, such as an index and middle finger, on a distal-facing surface of the flange extender 108. The barrel 104 and/or the flange extender 108 can also be grasped between a thumb and one or more finger. By moving the palm and/or thumb pad toward the barrel 104, the plunger 106 is moved into the barrel 104.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A syringe comprising: a barrel having an inner lumen and a flange extending radially from a proximal end portion of the barrel for facilitating handling of the syringe during operation; and a plunger having a plunger rod and a plunger head, the plunger rod having a distal end portion at least partially disposed within the inner lumen of the barrel and a proximal end portion coupled to the plunger head, the plunger head comprising proximal and distal-facing surfaces and a plurality of engagement structures extending distally from the distal-facing surface to facilitate gripping with a user's thumb during operation of the syringe.

Clause 2. The syringe of Clause 1, wherein a profile of the plunger head, transverse to a longitudinal axis of the plunger, is at least one of a circle, a square, and a rectangle.

Clause 3. The syringe of any one of Clauses 1 or 2, wherein the plurality of engagement structures are spaced apart and positioned around a longitudinal axis of the plunger to define a ring.

Clause 4. The syringe of any one of Clauses 1 to 3, wherein the plurality of engagement structures are positioned along a perimeter of the plunger head.

Clause 5. The syringe of any one of Clauses 1 to 4, wherein the plurality of engagement structures define a distal plane, and wherein a portion of the distal plane is concave.

Clause 6. The syringe of any one of Clauses 1 to 5, wherein the proximal-facing surface of the plunger head comprises a concave surface.

Clause 7. The syringe of any one of Clauses 1 to 6, wherein the plurality of engagement structures comprise protrusions.

Clause 8. The syringe of any one of Clauses 1 to 7, wherein the plurality of engagement structures comprise ridges that extend radially relative to a longitudinal axis of the plunger.

Clause 9. The syringe of any one of Clauses 1 to 8, wherein the plunger head comprises a first material and a second material, the second material being more flexible relative to the first material, and wherein the plurality of engagement structures comprises the second material.

Clause 10. The syringe of Clause 9, wherein a perimeter of the plunger head comprises the second material.

Clause 11. A syringe comprising: a barrel having a flange extending radially therefrom; a plunger disposed at least partially within the barrel; and a flange extender having a central body and opposing grip members extending radially from the central body, the central body having a proximal end, a distal end, and a longitudinal bore extending between the proximal and distal ends, the central body further comprising an engagement slot extending from a side surface of the central body into the longitudinal bore, and between the proximal and distal ends, to permit insertion thereinto of the barrel and the flange for facilitating removable coupling of the flange extender with the barrel.

Clause 12. The syringe of Clause 11, wherein the longitudinal bore comprises a flange bore and a barrel bore, the flange bore having a flange bore diameter, and the barrel bore having a barrel bore diameter that is smaller than the flange bore diameter.

Clause 13. The syringe of any one of Clauses 11 or 12, wherein the barrel bore diameter is approximately equal to or larger than a diameter of the barrel.

Clause 14. The syringe of any one of Clauses 11 to 13, wherein the barrel bore diameter is at least about 7.7 mm and/or less than or equal to about 11.5 mm.

Clause 15. The syringe of any one of Clauses 11 to 14, wherein a plunger bore extends through the proximal end of the central body to the longitudinal bore to permit insertion therethrough of a portion of the plunger.

Clause 16. The syringe of any one of Clauses 11 to 15, wherein a side aperture extends from the side surface of the central body, opposite the engagement slot, into the longitudinal bore.

Clause 17. The syringe of any one of Clauses 11 to 16, wherein the engagement slot comprises a flange slot and a barrel slot, and wherein, measured transversely relative to a longitudinal axis of the longitudinal bore, a width of the flange slot is larger than a width of the barrel slot.

Clause 18. The syringe of Clause 17, wherein the width of the barrel slot tapers from the side surface of the central body inwardly toward the longitudinal bore.

Clause 19. The syringe of any one of Clauses 17 to 18, wherein the flange slot comprises a height, measured parallel relative to the longitudinal axis of the longitudinal bore, that tapers from the side surface of the central body toward the longitudinal bore.

Clause 20. The syringe of Clause 19, wherein the height of the flange slot proximal to the side surface is at least about 1.8 mm and/or less than or equal to about 3.4 mm, and the height of the flange slot proximal to the longitudinal bore is at least about 1.7 mm and/or less than or equal to about 3.0 mm.

Clause 21. The syringe of any one of Clauses 17 to 20, wherein opposing inner surfaces of the engagement slot converge from a maximum width proximal to the side surface of the central body to a reduced width and then diverges to the maximum width proximal to the longitudinal bore.

Clause 22. The syringe of any one of Clauses 11 to 21, wherein the flange extender comprises opposing clip-on structures extending from opposing sections of the engagement slot to define a width that is less than a maximum diameter of the longitudinal bore, the clip-on structures providing an interference-based snap-on engagement with the barrel.

Clause 23. The syringe of any one of Clauses 11 to 22, wherein the flange extender comprises a first material and a second material, the second material being more flexible relative to the first material, and wherein an inner surface of any of the longitudinal bore and engagement slot comprises the second material.

Clause 24. The syringe of Clause 23, wherein a proximal-facing surface of the grip members comprises the second material.

Clause 25. The syringe of any one of Clauses 11 to 24, wherein: the barrel comprises an inner lumen, a proximal end portion, a distal end portion, the flange extending radially from the proximal end portion; and the plunger comprises a plunger rod and a plunger head, the plunger rod having a distal end portion at least partially disposed within the inner lumen of the barrel and a proximal end portion coupled to the plunger head.

Clause 26. The syringe of Clause 25, wherein the plunger head comprises proximal and distal-facing surfaces, the plunger head comprising a plurality of engagement structures extending distally from the distal-facing surface.

Clause 27. The syringe of Clause 26, wherein the plurality of engagement structures are spaced apart and positioned around a longitudinal axis of the plunger to define a ring.

Clause 28. The syringe of any one of Clauses 26 or 27, wherein the plurality of engagement structures are positioned along a perimeter of the distal-facing surface.

Clause 29. The syringe of any one of Clauses 26 to 28, wherein the plurality of engagement structures comprise dimples.

Clause 30. The syringe of any one of Clauses 26 to 29, wherein the plurality of engagement structures comprise protrusions.

Clause 31. The syringe of any one of Clauses 26 to 30, wherein the plurality of engagement structures comprise ridges that extend radially relative to a longitudinal axis of the plunger.

Clause 32. The syringe of any one of Clauses 26 to 31, wherein the plurality of engagement structures define a distal plane, and wherein a portion of the distal plane is concave.

Clause 33. The syringe of any one of Clauses 26 to 32, wherein the plunger head comprises a first material and a second material, the second material being more flexible relative to the first material, and wherein the plurality of engagement structures comprises the second material.

Clause 34. The syringe of Clause 33, wherein the proximal-facing surface of the plunger head comprises the second material.

Clause 35. The syringe of any one of Clauses 25 to 34, wherein a proximal-facing surface of the plunger head comprises a concave surface.

Clause 36. The syringe of any one of Clauses 25 to 35, wherein a profile of the plunger head, transverse to a longitudinal axis of the plunger, is at least one of a circle, a square, and a rectangle.

Clause 37. A method of assembling the syringe of any one of Clauses 11 to 36, comprising: inserting a flange of a proximal end portion of the barrel through the engagement slot such that the flange of the barrel is positioned within the longitudinal bore; and inserting a distal end portion of the plunger through the proximal end of the central body and into an inner lumen of the barrel.

Clause 38. The syringe of Clause 37, wherein inserting the flange of the barrel through the engagement slot comprises inserting the flange through a portion of the engagement slot comprising a flange slot.

Clause 39. The syringe of any one of Clauses 37 or 38, wherein inserting the distal end portion of the plunger through the proximal end of the central body comprises inserting a portion of the plunger having a plunger rod through a plunger bore of the central body.

Clause 40. A flange extender for coupling to a syringe, the flange extender comprising a central body and opposing grip members extending radially from the central body, the central body having a proximal end, a distal end, and a longitudinal bore extending between the proximal and distal ends, the central body further comprising an engagement slot extending from a side surface of the body into the longitudinal bore, and between the proximal and distal ends, to permit insertion thereinto of a barrel and a flange of a syringe for facilitating removable coupling of the flange extender with the syringe.

Clause 41. The syringe of Clause 40, wherein the longitudinal bore comprises a flange bore and a barrel bore, the flange bore having a flange bore diameter, and the barrel bore having a barrel bore diameter that is smaller than the flange bore diameter.

Clause 42. The syringe of any one of Clauses 40 or 41, wherein a plunger bore extends through the proximal end of the central body to the longitudinal bore to permit insertion therethrough of the plunger rod.

Clause 43. The syringe of any one of Clauses 40 to 42, wherein a side aperture extends from the side surface of the body, opposite the engagement slot, into the longitudinal bore.

Clause 44. The syringe of any one of Clauses 40 to 43, wherein the engagement slot comprises a flange slot and a barrel slot, and wherein, measured transversely relative to a longitudinal axis of the longitudinal bore, a width of the flange slot is larger than a width of the barrel slot.

Clause 45. The syringe of any one of Clauses 40 to 44, wherein the width of the barrel slot tapers from the side surface of the central body inwardly toward the barrel bore.

Clause 46. The syringe of any one of Clauses 40 to 45, wherein the flange slot comprises a height, measured parallel relative to the longitudinal axis of the longitudinal bore, that tapers from the side surface of the central body toward the longitudinal bore.

Clause 47. The syringe of any one of Clauses 40 to 46, wherein the flange extender comprises opposing clip-on structures extending from opposing sections of the engagement slot to define a width that is less than a maximum diameter of the longitudinal bore, the clip-on structures providing an interference-based snap-on engagement with the barrel.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The features of the present disclosure permit a user to retain the barrel 104 and/or the flange extender 108 between one or more fingers while performing an aspiration and ejection by moving the users thumb from a distal-facing surface of the plunger head 204 for aspiration, to a proximal-facing surface of the plunger head 204 for ejection.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A syringe plunger assembly, the assembly comprising:
    a plunger head comprising a distal-facing surface and a plurality of engagement structures extending distally from the distal-facing surface to facilitate gripping with a user's thumb during operation of the syringe; and
    a plunger rod having (i) a proximal end portion coupled to the distal-facing surface of the plunger head and (ii) a distal end portion configured to be at least partially disposed within a barrel of the syringe,
    wherein the plurality of engagement structures circumscribes the plunger rod.

2. The assembly of claim 1, wherein a profile of the plunger head, transverse to a longitudinal axis of the plunger, is at least one of a circle, a square, and a rectangle.

3. The assembly of claim 1, wherein the plurality of engagement structures are spaced apart and positioned around a longitudinal axis of the plunger to define a ring.

4. The assembly of claim 1, wherein the plurality of engagement structures are positioned along a perimeter of the plunger head.

5. The assembly of claim 1, wherein the plurality of engagement structures define a distal plane, and wherein a portion of the distal plane is concave.

6. The assembly of claim 1, wherein a proximal-facing surface of the plunger head comprises a concave surface.

7. The assembly of claim 1, wherein the plurality of engagement structures comprise protrusions.

8. The assembly of claim 1, wherein the plurality of engagement structures comprise ridges that extend radially relative to a longitudinal axis of the plunger.

9. The assembly of claim 1, wherein the plunger head comprises a first material and a second material, the second material being more flexible relative to the first material, and wherein the plurality of engagement structures comprises the second material.

10. The assembly of claim 9, wherein a perimeter of the plunger head comprises the second material.

* * * * *